United States Patent
Blain et al.

(10) Patent No.: US 10,568,664 B2
(45) Date of Patent: Feb. 25, 2020

(54) FLANGED INTERBODY FUSION DEVICE

(71) Applicant: Spinal Elements, Inc., Carlsbad, CA (US)

(72) Inventors: Jason Blain, Encinitas, CA (US); Bryan Hildebrand, Carlsbad, CA (US); Eric Kovach, Carlsbad, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 351 days.

(21) Appl. No.: 14/938,503

(22) Filed: Nov. 11, 2015

(65) Prior Publication Data

US 2016/0058481 A1   Mar. 3, 2016

Related U.S. Application Data

(62) Division of application No. 12/748,333, filed on Mar. 26, 2010, now Pat. No. 9,220,547.

(Continued)

(51) Int. Cl.
*A61B 17/70* (2006.01)
*A61F 2/44* (2006.01)
(Continued)

(52) U.S. Cl.
CPC ...... *A61B 17/7059* (2013.01); *A61B 17/8047* (2013.01); *A61F 2/447* (2013.01); *A61F 2002/2835* (2013.01); *A61F 2002/3008* (2013.01); *A61F 2002/3037* (2013.01); *A61F 2002/30062* (2013.01); *A61F 2002/3092* (2013.01); *A61F 2002/30392* (2013.01); *A61F 2002/30397* (2013.01); *A61F 2002/30398* (2013.01); *A61F 2002/30563* (2013.01); *A61F 2002/30578* (2013.01); *A61F 2002/30624* (2013.01); *A61F 2002/30637* (2013.01);
(Continued)

(58) Field of Classification Search
CPC .................................................. A61F 2/44–447
USPC .......................................... 623/17.11–17.16
See application file for complete search history.

(56) References Cited

U.S. PATENT DOCUMENTS 1,845,428 A   2/1932   Llewellyn
2,440,123 A   4/1948   Smith
(Continued)

FOREIGN PATENT DOCUMENTS

CA   1 329 525   5/1994
DE   30 27 138   12/1981
(Continued)

OTHER PUBLICATIONS

Official Communication in Australian Application No. 2014274519, dated Jun. 17, 2016.
(Continued)

*Primary Examiner* — Nicholas J Plionis
(74) *Attorney, Agent, or Firm* — Knobbe, Martens, Olson & Bear LLP

(57) ABSTRACT

Methods and devices are disclosed for treating the vertebral column. An implant for treating the spine is provided comprising at least two articulations between the spacer and the bone facing surface of the fixation plate. Another implant for treating the spine is also provided, comprising two or more fixation plates attached to a spacer with two or more articulations, wherein the fixation plates are independently movable.

24 Claims, 13 Drawing Sheets

Related U.S. Application Data

(60) Provisional application No. 61/164,029, filed on Mar. 27, 2009.

(51) Int. Cl.
*A61B 17/80* (2006.01)
*A61F 2/28* (2006.01)
*A61F 2/30* (2006.01)

(52) U.S. Cl.
CPC .............. *A61F 2002/30649* (2013.01); *A61F 2002/30777* (2013.01); *A61F 2002/30785* (2013.01); *A61F 2002/30789* (2013.01); *A61F 2002/30841* (2013.01); *A61F 2002/30904* (2013.01); *A61F 2002/30983* (2013.01); *A61F 2002/4475* (2013.01); *A61F 2210/0004* (2013.01); *A61F 2220/0025* (2013.01); *A61F 2220/0033* (2013.01); *A61F 2250/0098* (2013.01); *A61F 2310/00011* (2013.01); *A61F 2310/00023* (2013.01); *A61F 2310/0052* (2013.01); *A61F 2310/00179* (2013.01); *A61F 2310/00215* (2013.01); *A61F 2310/00221* (2013.01)

(56) References Cited

U.S. PATENT DOCUMENTS

| | | |
|---|---|---|
| 2,500,993 A | 3/1950 | Christopher |
| 2,677,369 A | 5/1954 | Knowles |
| 3,426,364 A | 2/1969 | Lumb |
| 3,848,601 A | 11/1974 | Ma et al. |
| 3,867,728 A | 2/1975 | Stubstad et al. |
| 3,893,196 A | 7/1975 | Hochman |
| 3,953,140 A | 4/1976 | Carlstrom |
| 3,987,499 A | 10/1976 | Scharbach et al. |
| 4,013,071 A | 3/1977 | Rosenberg |
| 4,309,777 A | 1/1982 | Patil |
| 4,349,921 A | 9/1982 | Kuntz |
| 4,388,921 A | 6/1983 | Sutter et al. |
| 4,401,112 A | 8/1983 | Rezaian |
| 4,464,090 A | 8/1984 | Duran |
| 4,484,570 A | 11/1984 | Sutter et al. |
| 4,554,914 A | 11/1985 | Kapp et al. |
| 4,599,086 A | 7/1986 | Doty |
| 4,834,757 A | 5/1989 | Brantigan |
| 4,892,545 A | 1/1990 | Day et al. |
| 4,904,261 A | 2/1990 | Dove et al. |
| 4,917,704 A | 4/1990 | Frey et al. |
| 4,955,908 A | 9/1990 | Frey et al. |
| 5,002,576 A | 3/1991 | Fuhrmann et al. |
| 5,053,036 A | 10/1991 | Perren et al. |
| 5,057,111 A | 10/1991 | Park |
| 5,085,660 A | 2/1992 | Lin |
| 5,147,361 A | 9/1992 | Ojima et al. |
| 5,176,709 A | 1/1993 | Branemark |
| 5,192,327 A | 3/1993 | Brantigan |
| 5,269,784 A | 12/1993 | Mast |
| 5,275,601 A | 1/1994 | Gogolewski et al. |
| 5,304,179 A | 4/1994 | Wagner |
| 5,306,307 A | 4/1994 | Senter et al. |
| 5,364,399 A | 11/1994 | Lowery et al. |
| 5,397,364 A | 3/1995 | Kozak et al. |
| 5,458,641 A | 10/1995 | Ramirez Jimenez |
| 5,474,555 A | 12/1995 | Puno et al. |
| 5,501,684 A | 3/1996 | Schlapfer et al. |
| 5,520,690 A | 5/1996 | Errico et al. |
| 5,522,899 A | 6/1996 | Michelson |
| 5,534,027 A | 7/1996 | Hodorek |
| 5,558,674 A | 9/1996 | Heggeness et al. |
| 5,578,034 A | 11/1996 | Estes |
| 5,607,426 A | 3/1997 | Ralph et al. |
| 5,607,428 A | 3/1997 | Lin |
| 5,609,635 A | 3/1997 | Michelson |
| 5,616,144 A | 4/1997 | Yapp et al. |
| 5,643,265 A | 7/1997 | Errico et al. |
| 5,665,089 A | 9/1997 | Dall et al. |
| 5,676,666 A | 10/1997 | Oxland et al. |
| 5,681,311 A | 10/1997 | Foley et al. |
| 5,713,900 A | 2/1998 | Benzel et al. |
| 5,735,853 A | 4/1998 | Olerud |
| 5,743,914 A | 4/1998 | Skiba |
| 5,755,796 A | 5/1998 | Ibo et al. |
| 5,807,396 A | 9/1998 | Raveh |
| 5,810,823 A | 9/1998 | Klaue et al. |
| 5,849,004 A | 12/1998 | Bramlet |
| 5,851,207 A | 12/1998 | Cesarone |
| 5,876,402 A | 3/1999 | Errico et al. |
| 5,888,223 A | 3/1999 | Bray |
| 5,902,303 A | 5/1999 | Eckhof et al. |
| 5,904,683 A | 5/1999 | Pohndorf et al. |
| 5,925,048 A | 7/1999 | Ahmad et al. |
| 5,931,838 A | 8/1999 | Vito |
| 5,951,558 A | 9/1999 | Fiz |
| 5,954,722 A | 9/1999 | Bono |
| 6,001,130 A | 12/1999 | Bryan et al. |
| 6,030,389 A | 2/2000 | Wagner et al. |
| 6,066,175 A | 5/2000 | Henderson et al. |
| 6,117,173 A | 9/2000 | Taddia et al. |
| 6,139,550 A | 10/2000 | Michelson |
| 6,152,927 A | 11/2000 | Farris et al. |
| 6,156,037 A | 12/2000 | Le Huec et al. |
| 6,193,721 B1 | 2/2001 | Michelson |
| 6,206,881 B1 | 3/2001 | Frigg et al. |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,261,291 B1 | 7/2001 | Talaber et al. |
| 6,273,889 B1 | 8/2001 | Richelsoph |
| 6,287,309 B1 | 9/2001 | Baccelli et al. |
| 6,302,883 B1 | 10/2001 | Bono |
| 6,306,136 B1 | 10/2001 | Baccelli |
| 6,306,139 B1 | 10/2001 | Fuentes |
| 6,306,170 B2 | 10/2001 | Rau |
| 6,318,602 B1 | 11/2001 | Michelson et al. |
| 6,331,179 B1 | 12/2001 | Freid et al. |
| 6,342,055 B1 | 1/2002 | Eisermann et al. |
| 6,383,186 B1 | 5/2002 | Michelson |
| 6,402,755 B1 | 6/2002 | Pisharodi |
| 6,413,259 B1 | 7/2002 | Lyons et al. |
| 6,428,542 B1 | 8/2002 | Michelson |
| 6,432,106 B1 | 8/2002 | Fraser |
| 6,454,769 B2 | 9/2002 | Wagner et al. |
| 6,461,359 B1 | 10/2002 | Tribus et al. |
| 6,503,250 B2 | 1/2003 | Paul |
| 6,508,818 B2 | 1/2003 | Steiner et al. |
| 6,565,570 B2 | 5/2003 | Sterett et al. |
| 6,575,975 B2 | 6/2003 | Brace et al. |
| 6,579,290 B1 | 6/2003 | Hardcastle et al. |
| 6,599,290 B2 | 7/2003 | Bailey et al. |
| 6,602,255 B1 | 8/2003 | Campbell et al. |
| 6,602,256 B1 | 8/2003 | Hayes |
| 6,605,090 B1 | 8/2003 | Trieu et al. |
| 6,613,053 B1 | 9/2003 | Collins et al. |
| 6,623,486 B1 | 9/2003 | Weaver et al. |
| 6,626,907 B2 | 9/2003 | Campbell et al. |
| 6,626,911 B1 | 9/2003 | Engman et al. |
| 6,645,208 B2 | 11/2003 | Apfelbaum et al. |
| 6,645,209 B2 | 11/2003 | Hall, IV et al. |
| 6,652,525 B1 | 11/2003 | Assaker et al. |
| 6,656,181 B2 | 12/2003 | Dixon et al. |
| 6,669,700 B1 | 12/2003 | Farris et al. |
| 6,679,883 B2 | 1/2004 | Hawkes et al. |
| 6,682,561 B2 | 1/2004 | Songer et al. |
| 6,682,563 B2 | 1/2004 | Scharf |
| 6,695,845 B2 | 2/2004 | Dixon et al. |
| 6,695,846 B2 | 2/2004 | Richelsoph et al. |
| 6,702,817 B2 | 3/2004 | Beger et al. |
| 6,730,127 B2 | 5/2004 | Michelson |
| 6,740,087 B2 | 5/2004 | Knox |
| 6,746,450 B1 | 6/2004 | Wall et al. |
| 6,755,833 B1 | 6/2004 | Paul et al. |

(56) References Cited

U.S. PATENT DOCUMENTS

| | | |
|---|---|---|
| 6,780,186 B2 | 8/2004 | Errico et al. |
| 6,884,242 B2 | 4/2005 | LeHuec et al. |
| 6,890,334 B2 | 5/2005 | Brace et al. |
| 6,890,335 B2 | 5/2005 | Grabowski et al. |
| 6,964,664 B2 | 11/2005 | Freid et al. |
| 6,984,234 B2 | 1/2006 | Bray |
| 7,001,389 B1 | 2/2006 | Navarro et al. |
| 7,025,769 B1 | 4/2006 | Ferree |
| 7,048,739 B2 | 5/2006 | Konieczynski et al. |
| 7,063,701 B2 | 6/2006 | Michelson |
| 7,077,844 B2 | 7/2006 | Michelson |
| 7,112,222 B2 | 9/2006 | Fraser et al. |
| 7,135,024 B2 | 11/2006 | Cook et al. |
| 7,172,627 B2 | 2/2007 | Fiere et al. |
| 7,186,254 B2 | 3/2007 | Dinh et al. |
| 7,220,263 B2 | 5/2007 | Cordaro |
| 7,232,464 B2 | 6/2007 | Mathieu et al. |
| 7,273,481 B2 | 9/2007 | Lombardo et al. |
| 7,306,605 B2 | 12/2007 | Ross |
| 7,309,340 B2 | 12/2007 | Fallin et al. |
| 7,481,829 B2 | 1/2009 | Baynham et al. |
| 7,481,830 B2 | 1/2009 | Wall et al. |
| 7,524,325 B2 | 4/2009 | Khalili |
| 7,547,324 B2 | 6/2009 | Cragg et al. |
| 7,621,943 B2 | 11/2009 | Michelson |
| 7,628,816 B2 | 12/2009 | Magerl et al. |
| 7,641,665 B2 | 1/2010 | Zubok et al. |
| 7,651,517 B2 | 1/2010 | Konieczynski et al. |
| 7,693,981 B2 | 4/2010 | Clubb et al. |
| 7,819,903 B2 | 10/2010 | Fraser et al. |
| 7,857,839 B2 | 12/2010 | Duong et al. |
| 7,914,561 B2 | 3/2011 | Konieczynski et al. |
| 7,931,840 B2 | 4/2011 | Michelson |
| 7,935,137 B2 | 5/2011 | Gorhan et al. |
| 7,963,981 B2 | 6/2011 | Binder et al. |
| 7,972,366 B2 | 7/2011 | Richelsoph et al. |
| 7,985,255 B2 | 7/2011 | Bray et al. |
| 8,100,955 B2 | 1/2012 | Blain et al. |
| 8,231,661 B2 | 7/2012 | Carls |
| 8,267,966 B2 | 9/2012 | McCormack et al. |
| 8,282,675 B2 | 10/2012 | Maguire et al. |
| 8,394,125 B2 | 3/2013 | Assell |
| 8,470,039 B2 | 6/2013 | Blain |
| 8,496,691 B2 | 7/2013 | Blain |
| 8,496,708 B2 | 7/2013 | Blain |
| 8,652,137 B2 | 2/2014 | Blain et al. |
| 8,696,721 B2 | 4/2014 | Blain |
| 8,740,942 B2 | 6/2014 | Blain |
| 8,801,794 B2 | 8/2014 | Blain |
| 9,101,410 B1 | 8/2015 | Urrea |
| 9,220,547 B2 | 12/2015 | Blain et al. |
| 9,265,546 B2 | 2/2016 | Blain |
| 9,271,765 B2 | 3/2016 | Blain |
| 9,585,707 B2 | 3/2017 | Blain |
| 9,936,984 B2 | 4/2018 | Blain |
| 2001/0007941 A1 | 7/2001 | Steiner et al. |
| 2001/0014807 A1 | 8/2001 | Wagner et al. |
| 2002/0004683 A1 | 1/2002 | Michelson |
| 2002/0016595 A1 | 2/2002 | Michelson |
| 2002/0022843 A1 | 2/2002 | Michelson |
| 2002/0045898 A1 | 4/2002 | Freid et al. |
| 2002/0147450 A1 | 10/2002 | LeHuec et al. |
| 2002/0151895 A1 | 10/2002 | Soboleski et al. |
| 2002/0169508 A1 | 11/2002 | Songer et al. |
| 2003/0093082 A1 | 5/2003 | Campbell et al. |
| 2003/0167091 A1 | 9/2003 | Scharf |
| 2003/0171753 A1 | 9/2003 | Collins et al. |
| 2003/0187442 A1 | 10/2003 | Richelsoph et al. |
| 2003/0199876 A1 | 10/2003 | Brace et al. |
| 2003/0212399 A1 | 11/2003 | Dinh et al. |
| 2004/0010254 A1 | 1/2004 | Cook et al. |
| 2004/0068319 A1 | 4/2004 | Cordaro |
| 2004/0087951 A1 | 5/2004 | Khalili |
| 2004/0097935 A1 | 5/2004 | Richelsoph et al. |
| 2004/0127900 A1 | 7/2004 | Konieczynski et al. |
| 2004/0127904 A1 | 7/2004 | Konieczynski et al. |
| 2004/0176778 A1 | 9/2004 | Zubok et al. |
| 2004/0181227 A1 | 9/2004 | Khalili |
| 2004/0210217 A1 | 10/2004 | Baynham et al. |
| 2004/0210219 A1 | 10/2004 | Bray |
| 2004/0220570 A1 | 11/2004 | Frigg et al. |
| 2004/0230192 A1 | 11/2004 | Graf |
| 2004/0260306 A1 | 12/2004 | Fallin et al. |
| 2005/0027296 A1 | 2/2005 | Thramann et al. |
| 2005/0033433 A1 | 2/2005 | Michelson |
| 2005/0049593 A1 | 3/2005 | Duong et al. |
| 2005/0085913 A1 | 4/2005 | Fraser et al. |
| 2005/0101960 A1 | 5/2005 | Fiere et al. |
| 2005/0277933 A1 | 5/2005 | Wall et al. |
| 2005/0149191 A1 | 7/2005 | Cragg et al. |
| 2005/0159746 A1 | 7/2005 | Grab et al. |
| 2005/0177245 A1 | 8/2005 | Leatherbury et al. |
| 2005/0192576 A1 | 9/2005 | Michelson |
| 2006/0122604 A1 | 6/2006 | Gorhan et al. |
| 2006/0200147 A1 | 9/2006 | Ensign et al. |
| 2006/0235403 A1 | 10/2006 | Blain |
| 2006/0235409 A1 | 10/2006 | Blain |
| 2006/0235418 A1 | 10/2006 | Gil et al. |
| 2006/0235533 A1* | 10/2006 | Blain ................. A61B 17/7059 623/17.16 |
| 2006/0241597 A1 | 10/2006 | Mitchell et al. |
| 2006/0241616 A1 | 10/2006 | Konieczynski et al. |
| 2006/0247650 A1* | 11/2006 | Yerby ................. A61B 17/025 606/90 |
| 2007/0055252 A1 | 3/2007 | Blain et al. |
| 2007/0055373 A1 | 3/2007 | Hudgins et al. |
| 2007/0123863 A1 | 5/2007 | Winslow et al. |
| 2007/0135814 A1 | 6/2007 | Farris |
| 2007/0213820 A1 | 9/2007 | Magerl et al. |
| 2007/0250166 A1 | 10/2007 | McKay |
| 2008/0103598 A1 | 5/2008 | Trudeau et al. |
| 2008/0161925 A1* | 7/2008 | Brittan ................. A61F 2/4465 623/17.16 |
| 2008/0177390 A1* | 7/2008 | Mitchell ................. A61F 2/442 623/17.16 |
| 2009/0270929 A1 | 10/2009 | Suddaby |
| 2010/0070037 A1 | 3/2010 | Parry et al. |
| 2010/0249937 A1 | 9/2010 | Blain et al. |
| 2011/0015744 A1 | 1/2011 | Squires et al. |
| 2012/0046749 A1 | 2/2012 | Tatsumi |
| 2012/0277801 A1 | 11/2012 | Marik et al. |
| 2013/0123923 A1 | 5/2013 | Pavlov et al. |
| 2013/0197646 A1 | 8/2013 | Blain |
| 2013/0253590 A1 | 9/2013 | Blain |
| 2014/0012318 A1 | 1/2014 | Goel |
| 2014/0066758 A1 | 3/2014 | Marik et al. |
| 2014/0336768 A1 | 11/2014 | Blain |
| 2015/0342648 A1 | 12/2015 | McCormack et al. |
| 2016/0213481 A1 | 7/2016 | Blain |
| 2017/0189077 A1 | 7/2017 | Blain |

FOREIGN PATENT DOCUMENTS

| | | |
|---|---|---|
| DE | 30 27 148 | 12/1981 |
| DE | 297 01 099 | 4/1997 |
| DE | 197 02 201 | 8/1998 |
| DE | 20 2004 015 912 | 12/2004 |
| EP | 0 242 842 | 10/1987 |
| EP | 0 974 319 | 1/2000 |
| EP | 1 346 697 | 9/2003 |
| EP | 1 470 803 | 10/2004 |
| FR | 2 766 353 | 1/1999 |
| FR | 2 859 904 | 3/2005 |
| JP | 2002-515287 | 5/2002 |
| JP | 2003-518977 | 6/2003 |
| JP | 2004-500156 | 1/2004 |
| WO | WO 88/003781 | 6/1988 |
| WO | WO 89/004150 | 5/1989 |
| WO | WO 93/010725 | 6/1993 |
| WO | WO 94/000066 | 1/1994 |
| WO | WO 95/035067 | 12/1995 |
| WO | WO 00/024343 | 5/2000 |
| WO | WO 01/003570 | 1/2001 |

(56) References Cited

FOREIGN PATENT DOCUMENTS

| WO | WO 01/049191 | 7/2001 |
|---|---|---|
| WO | WO 01/078615 | 10/2001 |
| WO | WO 01/089428 | 11/2001 |
| WO | WO 03/017856 | 3/2003 |
| WO | WO 03/071966 | 9/2003 |
| WO | WO 2004/006792 | 1/2004 |
| WO | WO 2005/027760 | 3/2005 |
| WO | WO 2006/020464 | 2/2006 |

OTHER PUBLICATIONS

Official Communication in Australian Application No. 2014274519, dated Aug. 26, 2016.
Notice of Acceptance in Australian Application No. 2014274519, dated Sep. 22, 2016.
Official Communication in Australian Application No. 2016277588, dated Sep. 7, 2017.
Official Communication in European Application No. 14190344.3, dated Jan. 4, 2016.
Official Communication in European Application No. 14190344.3, dated Sep. 8, 2016.
International Search Report and Written Opinion in International Application No. PCT/US2016/013062, dated Mar. 16, 2016.
International Preliminary Report on Patentability and Written Opinion in International Application No. PCT/US2016/013062, dated Aug. 10, 2017.
Official Communication in Australian Application No. 2006227755, dated Dec. 8, 2010.
Official Communication in Australian Application No. 2012211502, dated Jul. 17, 2013.
Notice of Acceptance in Australian Application No. 2012211502, dated Sep. 10, 2014.
Official Communication in European Application No. 06738204.4, dated Mar. 26, 2009.
Official Communication in European Application No. 06738204.4, dated Apr. 6, 2010.
Official Communication in European Application No. 06738204.4, dated Apr. 5, 2011.
Official Communication in European Application No. 06738204.4, dated Oct. 28, 2011.
Official Communication in European Application No. 06738204.4, dated Jul. 18, 2012.
Official Communication in European Application No. 06738204.4, dated Oct. 14, 2013.
Extended European Search Report for European Application No. 11160061.5, dated Nov. 2, 2011.
Official Communication in European Application No. 11160061.5, dated Sep. 9, 2012.
Extended European Search Report for European Application No. 11160063.1, dated Nov. 2, 2011.
Official Communication in European Application No. 11160063.1, dated Jul. 12, 2012.
Official Communication in European Application No. 11160063.1, dated Nov. 27, 2012.
Official Communication in European Application No. 11160063.1, dated Oct. 14, 2013.
Official Communication in Japanese Application No. 2008-501962, dated May 10, 2011.
Official Communication in Japanese Application No. 2008-501962, dated Nov. 13, 2012.
Official Communication in Japanese Application No. 2011-210533, dated Mar. 5, 2013.
Official Communication in Japanese Application No. 2011-210533, dated Dec. 3, 2013.
Notice of Allowance in Japanese Application No. 2011-210533, dated May 7, 2014.
Notice of Allowance in Japanese Application No. 2013-117602, dated May 7, 2014.
International Search Report and Written Opinion in International Application No. PCT/US2006/009120, dated Oct. 20, 2006.
International Preliminary Report and Written Opinion in International Application No. PCT/US2006/009120, dated Sep. 18, 2007.
Official Communication in Australian Application No. 2014274519, dated Sep. 17, 2015.
Official Communication in European Application No. 14190344.3, dated Feb. 10, 2015.
Official Communication in European Application No. 18150661.9, dated May 25, 2018.
Official Communication in European Application No. 16743832.4, dated Jul. 24, 2018.

* cited by examiner

FLANGED INTERBODY FUSION DEVICE

CROSS-REFERENCE TO RELATED APPLICATIONS

This application is a divisional of U.S. patent application Ser. No. 12/748,333, filed Mar. 26, 2010, which claims priority under 35 U.S.C. § 119(e) to U.S. Provisional Patent Application No. 61/164,029 filed on Mar. 27, 2009, the disclosure of each is incorporated by reference herein in its entirety.

BACKGROUND OF THE INVENTION

Field of the Invention

This invention relates generally to systems and methods for performing spinal fixation and, in particular, to interbody spacer devices.

Description of the Related Art

Advancing age, as well as injury, can lead to degenerative changes in the bones, discs, joints and ligaments of the spine, producing pain and instability. Under certain circumstances, alleviation of the problems can be provided by performing spinal fusion. Spinal fusion is a surgical technique where two or more vertebrae of the spinal column are fused together to eliminate the motion between the fused vertebrae. Spinal fusion is used to treat conditions where the spine exhibits instability. Spine instability may result from causes such as fracture, scoliosis and spondylolisthesis, where one or more vertebrae move in a forward direction relative to the other vertebrae. Spinal fusion with discectomy is also performed for herniations of the discs. This surgery involves removal of the affected disc and fusion of the adjacent vertebrae. Traditionally, bone grafts have been used to fuse the vertebrae, but various types of vertebral implants have also been used.

The use of bone plate and bone screw fixation systems for treating injuries to bones is well established. In most instances, a bone plate is positioned over and surrounding the bone injury area and secured to the bone. The bone plate is secured to the bone by bone screws or other similar fasteners inserted through holes in the bone plate and into the bone itself. The screws are tightened so that the bone plate holds the bone to be treated in place in order to insure proper healing. Early fixation devices tended to be applicable only to long bone injuries with only limited uses for lower lumbar spinal injuries and disorders. The use of plate/screw fixation systems later expanded, however, to include more uses for spinal injuries, including fusion of vertebrae including fixation devices for treating cervical vertebrae injuries. Notwithstanding the foregoing, there remains a need for improved methods and devices for treating spinal instability.

In existing spinal fusion implants there have also been problems with loosening and backing out of screws, especially in the cervical vertebrae where the screws can back out into the patient's throat area. Backout is the exhibited tendency of bone screws, which affix the bone plate to the bone(s), to loosen with respect to both the plate and bone, resulting in poor fixation, fusion and ultimately, healing. Essentially, this loosening of the bone screw causes the screw to work itself out of the bone into which it is implanted. This results in the bone plate being poorly fixed in place thus becoming devoid of its fixation capabilities. Usually, backout is caused by the chronic stress of bodily movement. While such loosening can be benign if limited in scope, it can lead to complications such as complete failure of the fixation device or incomplete bone fusion. Backout is particularly prevalent in areas of high bodily stress and movement, such as the spine.

To alleviate backout and its associated problems, current systems utilize secondary locking screws, locking collars or other secondary locking devices that hold the bone screws in place after deployment within the bone. In most systems, the bone screw is affixed into the bone through an opening in a bone plate. A locking device is then inserted into the bone screw. The locking device engages the head of the bone screw and is tightened which results in the bone screw being fixed in place within the bone, thus preventing backout.

While a locking screw or collar can alleviate backout, successful use of such locking device systems in the anterior cervical spine is particularly difficult because of anatomic constraints. Systems using multiple types of screws or collars to hold the bone screw in place are difficult to deploy within the confines of a small operating area available at the cervical spine. Furthermore, due to the small operating area, the surgeon implanting the device has great difficulty determining if the device is properly deployed. Any instrumentation implanted in the region must be minimally intrusive, yet have adequate strength to withstand the biomechanical loads to which it will be subjected. Thus, while current systems can help reduce instances of backout, their complex nature makes proper deployment very difficult and increases the chance of surgical error.

There is a need for an implant having a locking mechanism that can be easily and reliably locked in place to prevent the loosening of and backing out of the bone screws used to attach the implant to the vertebrae in the anterior aspect of the cervical, thoracic, and lumbar spine.

There is also a need for implants that can be implanted along a series of adjacent vertebrae. Implants adapted for use in the lumbar spine and the thoracic spine become much less usable in the cervical spine because of differences in anatomy. In the lumbar spine, the disc spaces are about 25% as tall as the vertebral bodies (i.e., the vertebral bodies are generally four times taller than the intervening disc space). In the cervical spine, the disc space can be 50% of the height of the vertebral bodies. The disc spaces in the cervical spine are generally not greater than 7 or 8 mm tall in most people.

Attachment of one fixation plate between two vertebrae often prevents the attachment of additional fixation plates between one of two vertebrae and an adjacent vertebra. This is especially true in the cervical spine region. The attachment of one fixation plate will reduce the surface area available to attach another fixation plate due to the small size of the cervical vertebrae and the minimum size required for each fixation plate. Because of this limitation in existing spinal fixation devices, treatment of spinal disorders may be suboptimal because disease in adjacent vertebrae cannot be treated adequately.

SUMMARY OF THE INVENTION

Devices and methods are disclosed for treating the vertebral column. An integrated fixation plate and spacer is provided with at least two articulations between the fixation plate and spacer. In some embodiments, an implant for treating the spine is provided comprising a fixation plate having an access surface and a bone facing surface, an upper portion and a lower portion, a spacer, and at least two articulations between the spacer and the bone facing surface of the fixation plate. In some embodiments, the at least two articulations provide for pivotable articulation and anterior-posterior movement between the spacer and the fixation plate.

In some embodiments, an implant for treating the spine is provided, comprising two or more fixation plates, a spacer, and two or more articulations between the spacer and the two or more fixation plate, wherein the two or more fixation plates are independently movable.

In some embodiments, a method for treating a spine is provided, comprising: providing an implant for treating the spine comprising a first and a second fixation plates, a spacer, and a first and a second articulations between the spacer and the first and the second fixation plates, wherein the fixation plates are independently movable, inserting the spacer into an intervertebral space between a first vertebra and a second vertebra, positioning the first fixation plate to lie generally flat on the first vertebra, attaching the first fixation plate to the first vertebra, positioning the second fixation plate in generally the opposite direction as the first fixation plate to lie generally flat on the second vertebra, and attaching the second fixation plate to the second vertebra.

The above embodiments and methods of use are explained in more detail below.

BRIEF DESCRIPTION OF THE DRAWINGS

The structure and method of using the invention will be better understood with the following detailed description of embodiments of the invention, along with the accompanying illustrations, in which.

DETAILED DESCRIPTION OF THE PREFERRED EMBODIMENTS

A. Anatomy of the Spine

Figure 1:
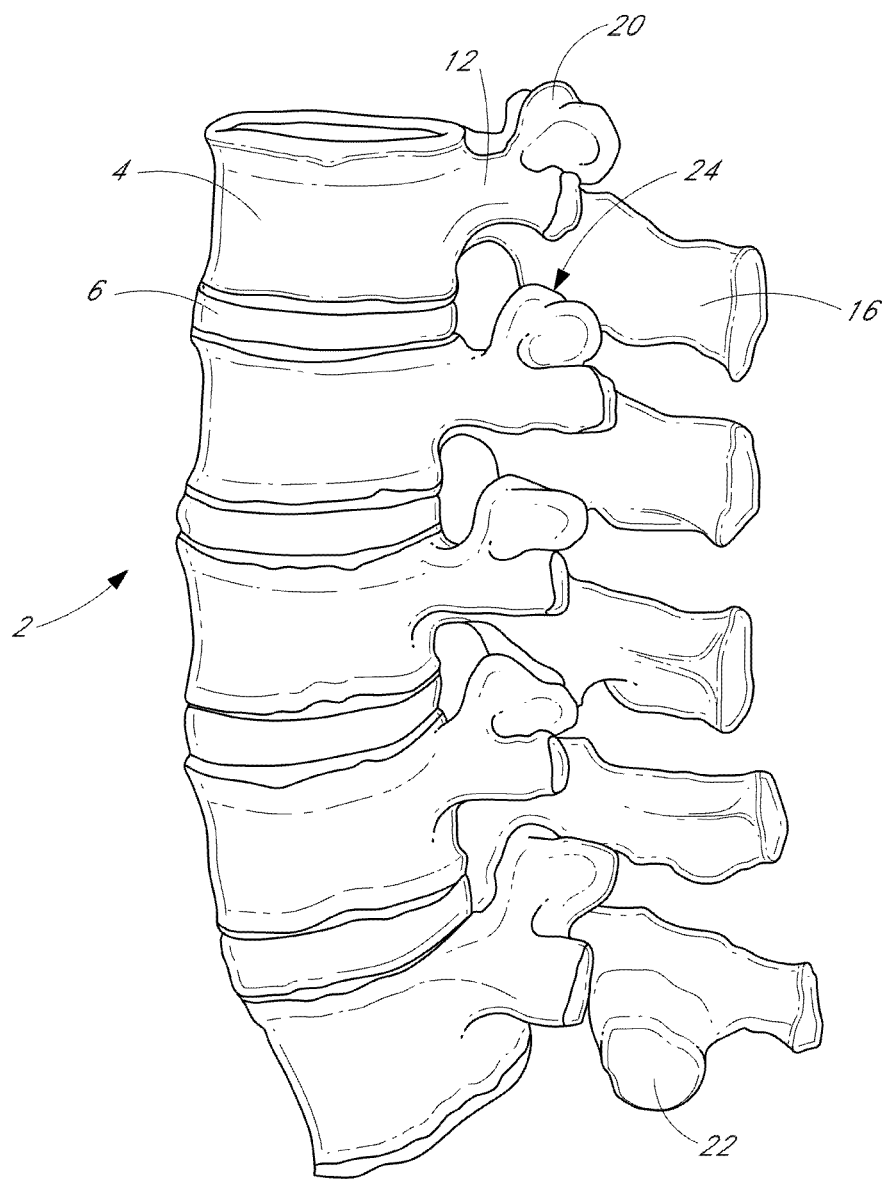
FIG. 1 is a lateral elevational view of a portion of the vertebral column.
Figure 2A:
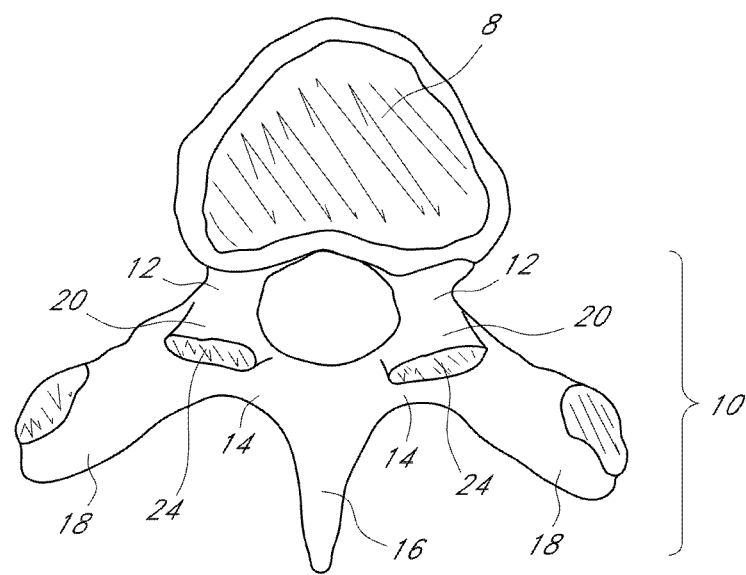
FIGS. 2A and 2B are superior and lateral elevational views of a thoracic vertebra.
Figure 2B:
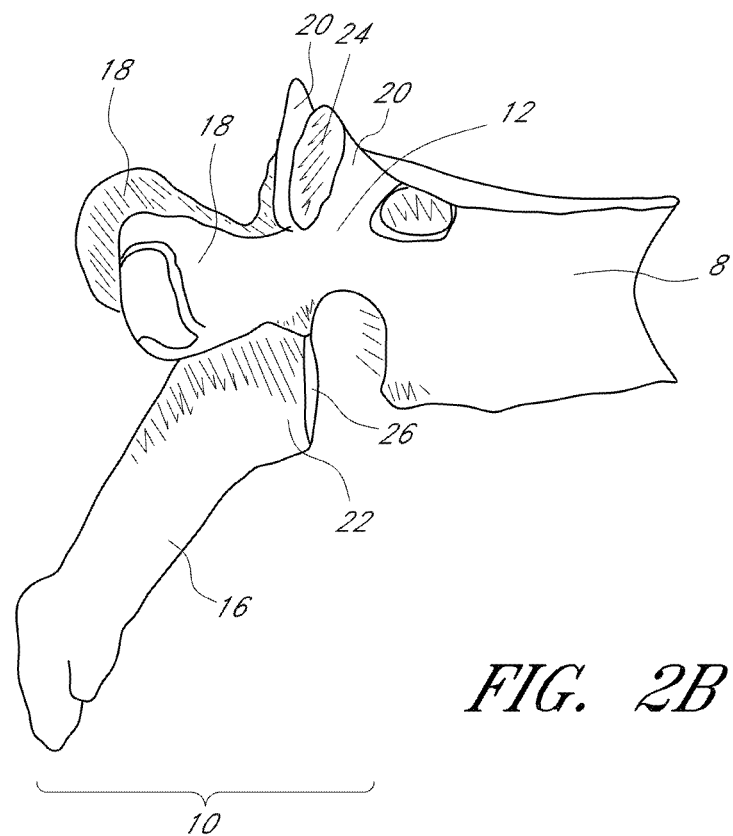

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 with the articular processes of the adjacent vertebrae.

Figure 3:
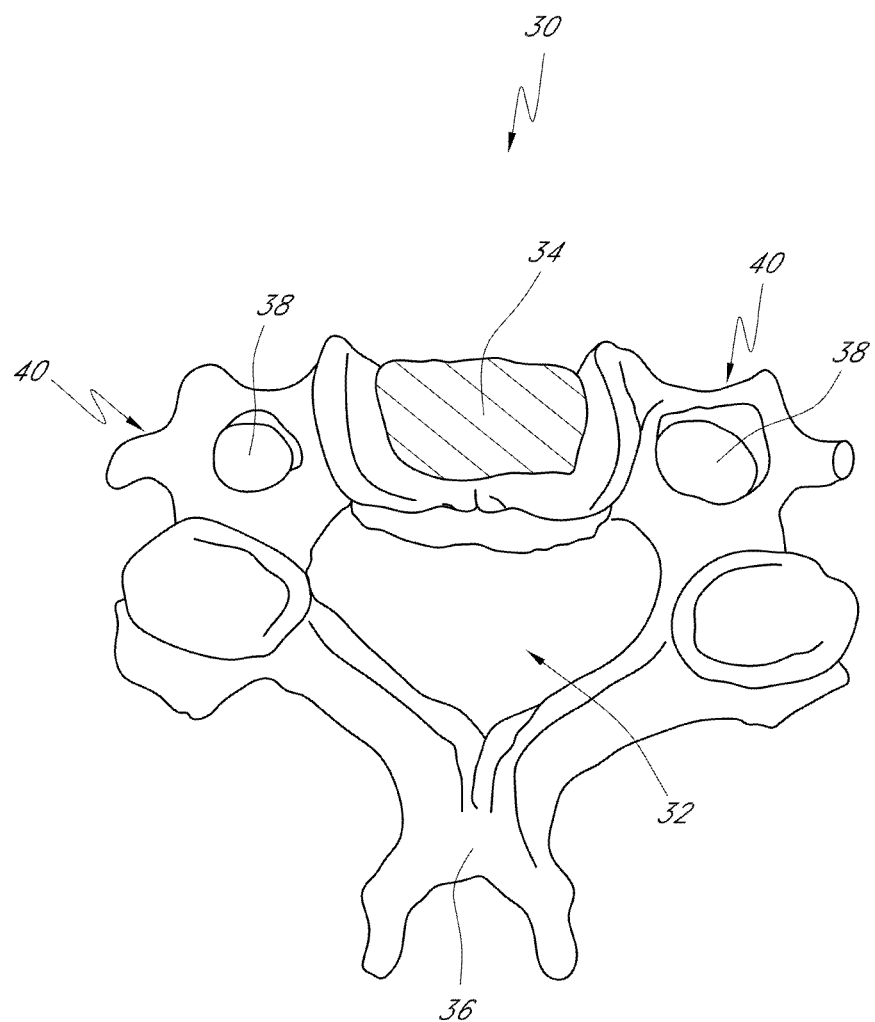
FIG. 3 illustrates a superior elevational view of a cervical vertebra.

The typical cervical vertebrae 30, shown in FIG. 3, differ from the other vertebrae with relatively larger spinal canals 32, oval shaped vertebral bodies 34, bifid spinous processes 36 and foramina 38 in their transverse processes 40. These foramina transversaria 38 contain the vertebral artery and vein. The first and second cervical vertebrae also further differentiated from the other vertebrae. The first cervical vertebra lacks a vertebral body and instead contains an anterior tubercle. Its superior articular facets articulate with the occipital condyles of the skull and are oriented in a roughly parasagittal plane. The cranium is able to slide forward and backwards on this vertebra. The second cervical vertebra contains an odontoid process, or dens, which projects superiorly from its body. It articulates with the anterior tubercle of the atlas, forming a pivot joint. Side to side movements of the head occur at this joint. The seventh cervical vertebra is sometimes considered atypical since it lacks a bifid spinous process.

Figure 4:
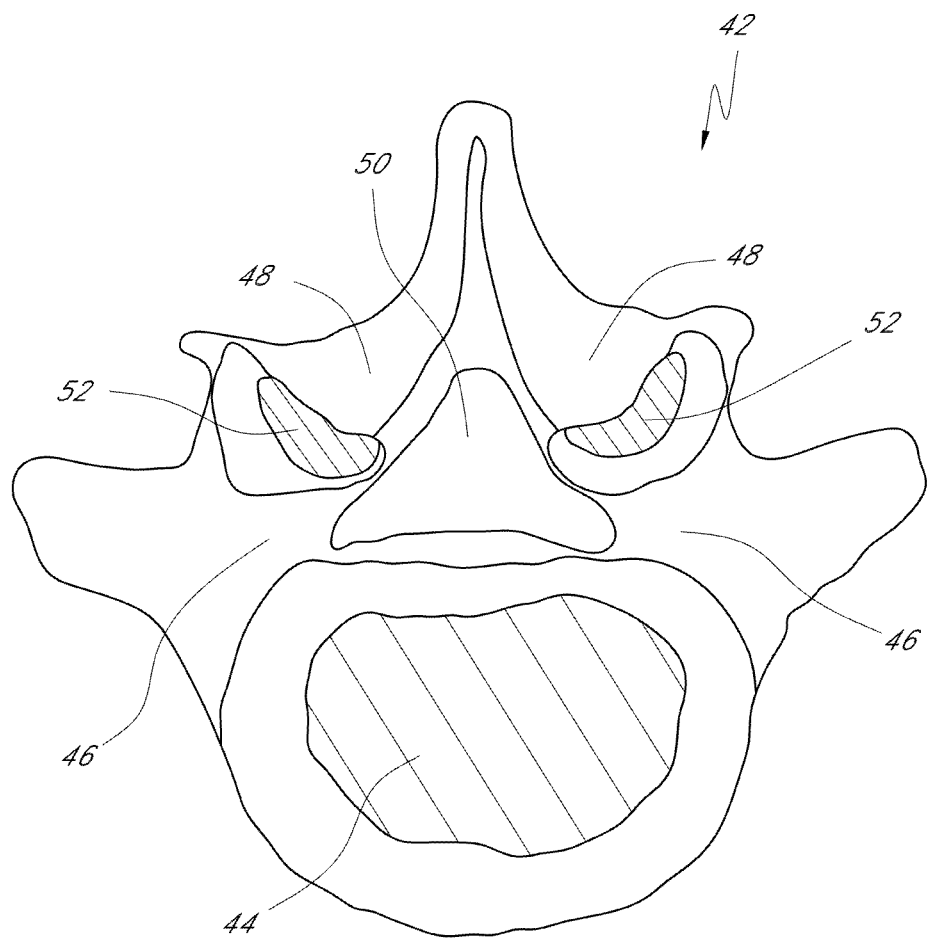
FIG. 4 represents a superior elevational view of a lumbar vertebra.
Figure 5A:
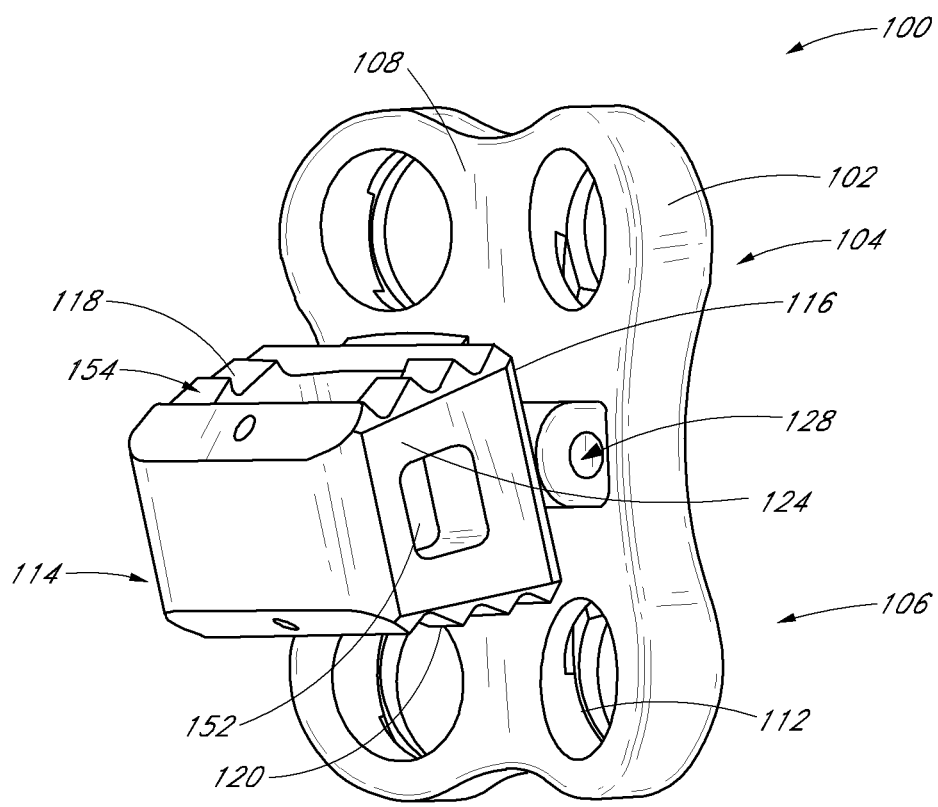
FIGS. 5A to 5D are various views of an embodiment of a pivotal fixation plate and spacer device.
Figure 5B:
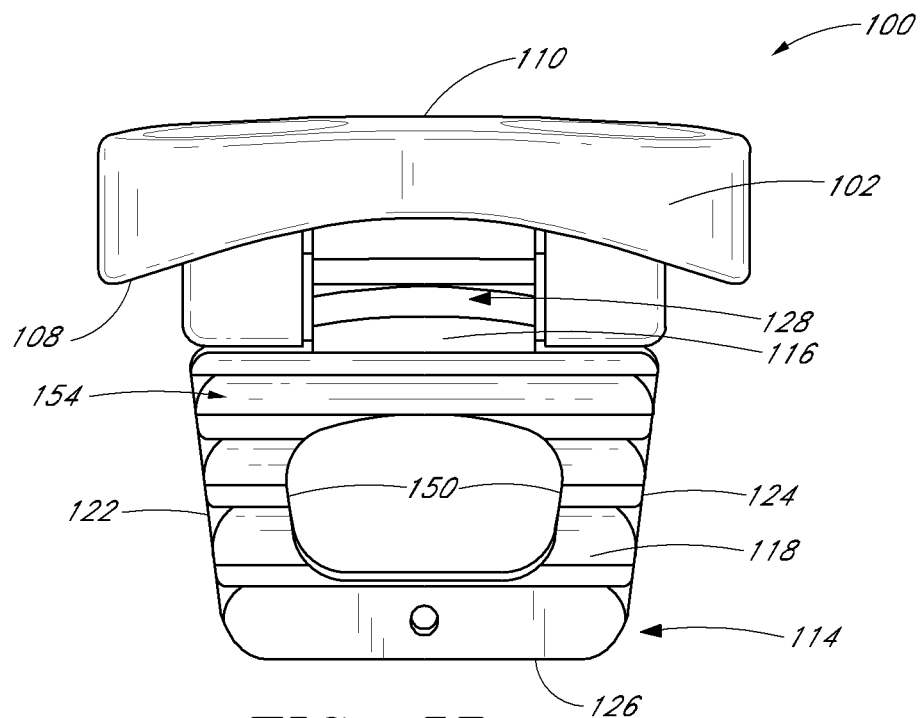
Figure 5C:
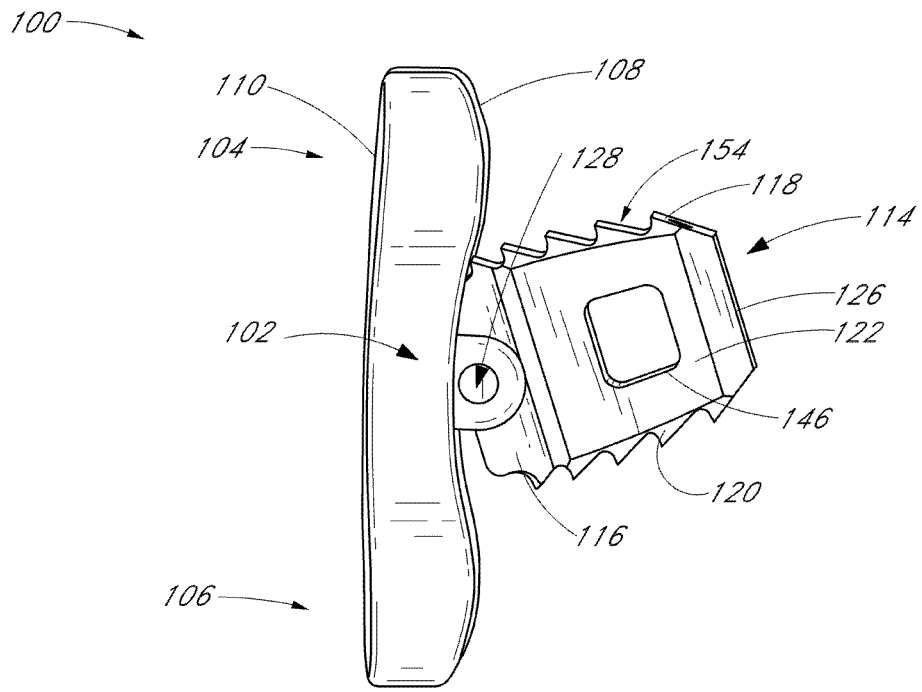
Figure 5D:
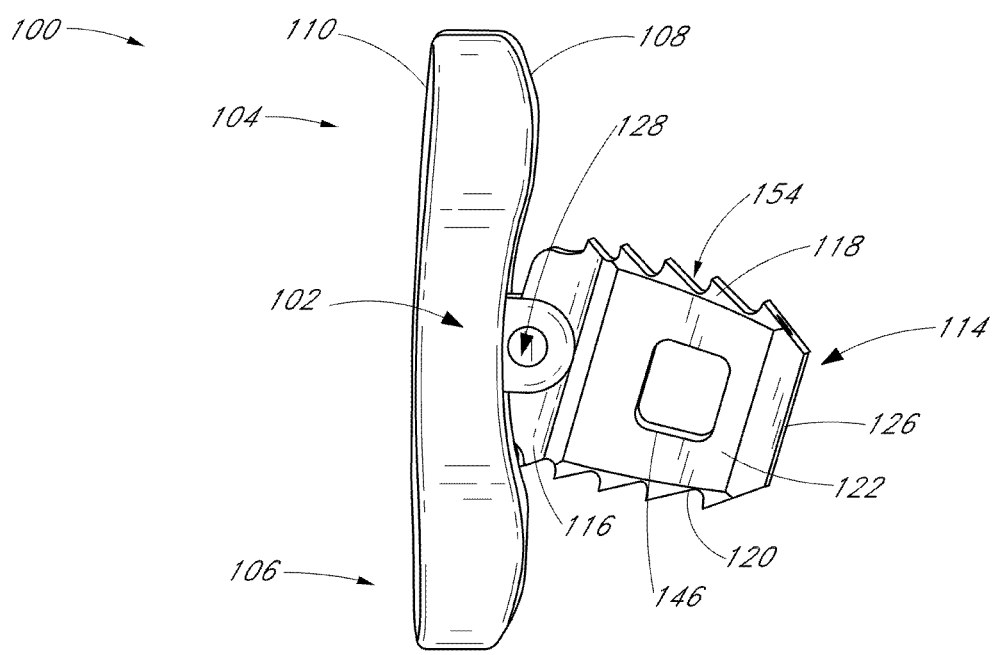

Referring to FIG. 4, the typical lumbar vertebrae 42 is distinguishable from the other vertebrae by the absence of foramina transversaria and the absence of facets on the surface of the vertebral body 44. The lumbar vertebral bodies 44 are larger than the thoracic vertebral bodies and have thicker pedicles 46 and laminae 48 projecting posteriorly. The vertebral foramen 50 is triangular in shape and larger than the foramina in the thoracic spine but smaller than the foramina in the cervical spine. The superior 52 and inferior articular processes (not shown) project superiorly and inferiorly from the pedicles, respectively.

B. Flanged Spacer

In some embodiments, an interbody vertebral implant 100 can be provided. As shown in FIGS. 5A through 5D, in some embodiments, the implant 100 can comprise a stabilization or fixation plate 102 having an upper portion 104 and a lower portion 106, and a bone facing surface 108 and an access surface 110. In use, typically the bone facing surface 108 can actually contact the vertebral bone surface, but in other embodiments, other structures or components can lie in between the bone facing surface 108 and the bone surface of the vertebra. Each upper portion 104 and lower portion 106 can have one or more spaces or holes 112 oriented between the bone facing surface 108 and the access surface 110 that are configured to accept screws and/or other attachment devices for anchoring the implant 100 to the vertebral bone. One or more spacers or spacing structures 114 can be located on the bone facing surface 108 of the fixation plate 102. The spacers 114 can be typically integrated with the fixation plate 102 about the bone facing surface 108.

1. Spacer Component

The spacer can comprise any structure configured to maintain a separation and resist compression between two adjacent vertebral bodies. The spacer can have any of a variety of overall shapes, including but not limited to a rectangular box, a trapezoidal box, H-shaped, O-shaped, V-shaped, with or without one or more lumens within the spacing structure. As shown in FIGS. 5A through 5D, the spacer 114 can have a base 116, a superior surface 118 and an inferior surface 120, and side surfaces 122, 124, and a posterior surface 126. Each surface 118, 120, 122, 124, 126 need not be flat, and can be curved or undulating or any combination thereof. The upper and lower surfaces 118, 120 can be configured for facing the superior and inferior vertebral bodies 8 or 34 adjacent to an implantation site. The relative configuration of the upper surface 118 and lower surface 120 can vary, depending upon the relative position desired between the two adjacent vertebrae, the anatomical shape of the vertebrae, ease of insertion of the implant and other factors. For example, if a neutral vertical alignment is desired between two vertebrae, the upper and lower surfaces 118, 120 can have generally parallel planar orientations. If a non-neutral alignment is desired, for instance to maintain a natural spinal curvature in the cervical region, the upper and lower surfaces 118, 120 can have a wedge-like relationship to allow fixation of the vertebrae in the desired non-neutral position. A non-neutral alignment with respect to the anterior-posterior direction can also be used to compensate for excessive lordosis or kyphosis in other portions of the vertebral column. The height of the spacing structure 114 at any section between the upper and lower surfaces 118, 120 can be further configured to accommodate degenerative changes or anatomical anomalies to provide fixation in the desired relative position. Likewise, the side surfaces 122, 124 of the spacing structure 114 can be generally parallel or skewed. In some embodiments, the side surfaces 122, 124 of the implant 100 taper with increasing distance from the base 116 of the implant 100. A tapered spacing structure can facilitate insertion of the implant 100 into the intervertebral space. In other embodiments, the one or more side surfaces can flare distally or have both tapering and flaring portions.

FIGS. 5A through 5D illustrate an embodiment comprising a spacer 114 with windows or holes 146, 152 between the outer side surfaces 122, 124 and inner side surface 150 of the posterior member. These windows or holes can allow bony growth into the windows or holes. The space 146, 152 within and/or between the posterior members can also be filled with graft materials (not shown). The graft material can be an autograft, allograft, xenograft or synthetic material. Synthetic graft material can be ceramic-based, silicon-based or calcium-based. The graft material can also include osteoinductive factors to promote bone ingrowth. One skilled in the art will appreciate that there are many varieties of synthetic graft materials and constituents that can be used between or about the hyoid bone segments.

One or more surfaces of the implant can also have surface projections, indentations, or holes or pores that can further alter the characteristics of the implant. Referring to FIGS. 5A through 5D, in some embodiments, angled projections, barbs, teeth 154 or ramped surfaces which incline outwardly from one or more spacer surfaces toward the fixation plate 102 can be provided on one or more surfaces that allow insertion of the spacing structure in one direction but resist movement in the opposite direction. These teeth 154 can be advantageous in reducing the migration of the device out of the intervertebral space. Improved fixation of the spacer 114 can maintain device position during drilling of the screw holes into the vertebral bodies, and can also reduce the forces acting upon the screws or other retaining structures, thereby reducing the risk of backout. The teeth 154 are preferably provided on the superior and/or inferior surfaces 118, 120 of the spacer 114, but other surfaces can also have teeth or other tissue engagement structures.

In some embodiments, the tissue engagement structures can be combined with indentations, holes or pores for allowing bony ingrowth or filling with bony matrix or graft materials as previously described. These holes can be utilized with other surface features to further enhance insertion and stabilization of the implant.

In some embodiments, the spacer can have a height of about 4 mm to about 50 mm, or preferably about 4 mm to about 12 mm. In some embodiments, the spacer can have a height of about 6 mm to about 9 mm. In some embodiments, the spacer can have a length as measured from the bone facing surface of the fixation plate to the most posterior end of the spacer of about 5 mm to about 25 mm. In some embodiments, the spacer length can be about 10 mm to about 15 mm. The width of the spacer can be generally about 5 mm to about 25 mm, and in some situations, about 10 mm to about 15 mm. One skilled in the art can dimension the spacer based upon the implantation location and specific vertebral morphology, neurological anatomy and disease state.

The spinal fusion implant can include, be made of, treated, coated, filled, used in combination with, or contain artificial or naturally occurring materials suitable for implantation in the human spine. These materials can include any source of osteogenesis, bone growth-promoting materials, bone derived substances, bone morphogenetic proteins, hydroxyapatite, genes coding for the production of bone, and bone including, but not limited to, cortical bone. The implant can also be formed of material such as metal including, but not limited to, titanium and its alloys, surgical grade plastics, plastic composites, ceramics, or other materials suitable for use as a spinal fusion implant. In some embodiments, the device can comprise a radiolucent material, a radio-opaque material, or a combination thereof. A device that is partially or completely radiolucent can be advantageous when evaluating the effect of the implant post-implantation. Many existing spinal fixation plates and/or spacers obscure visualization of the vertebrae, which can complicate post-operative treatment, diagnosis and prognosis of the patient's condition. The implant can include at least in part materials that are bioabsorbable in the body. The implant of the described embodiments can be formed of a porous material or can be formed of a material that intrinsically participates in the growth of bone from one of adjacent vertebral bodies to the other of adjacent vertebral bodies. The implant can be treated with, coated with, or used in combination with substances to inhibit scar tissue formation. The implant of the described embodiments can be modified, or used in combination with materials to provide antibacterial properties, such as, but not limited to, electroplating or plasma spraying with silver ions or other substance. The implant can optionally comprise an electrical source to provide ionophoresis of the silver ions into the surrounding tissue to prevent infection. The antibacterial properties can include bactericidal and/or bacteriostatic characteristics. Similarly, anti-fungal characteristics can also be provided. Any of these materials as appropriate can be used at any time after the implant(s) are inserted.

2. Fixation Component

The fixation plate can have a generally flat configuration, curved configuration or combination thereof. Optionally, each surface of the fixation plate can also have a generally flat or curved configuration or combination thereof. Each surface of the fixation plate need not have the same configuration. The edges of the fixation plate can optionally be rounded, smoothed or polished. In some embodiments, the flange can be dimensioned such that the flange extends about 2 mm beyond the edges of the base of the spacer. In some embodiments, the fixation component can be dimensioned to extend generally about 1 mm to about 20 mm beyond the perimeter of the spacer component at its interface with the fixation plate. In other embodiments, the flange can extend by 3 mm or 4 mm or more beyond the spacer base. The flange may or may not extend uniformly along the spacer edges. The shape of the flange can be different from the shape of the spacer base.

In some embodiments, illustrated in FIGS. 5A through 5D, the flange 102 of implant 100 can have a general square or rectangular shape and is dimensioned to allow stable attachment of the implant 100 to the adjacent vertebral bodies 8. The corners where any two sides of the flange meet can be angled, rounded or curved. The flanged implant 100 depicted in FIGS. 5A through 5D can comprise rounded corners. In other embodiments, the flange 102 can comprise any of a variety of other shapes, including trapezoids, circles, ovals, polygons or other closed shapes. The flange 102 may or may not have a symmetrical configuration with respect the upper and lower portions and/or the left and right portions of the flange.

In some embodiments, the average thickness of the fixation plate can be within the range of about 1 mm to about 5 mm. In other embodiments, the average thickness of the fixation plate can be within the range of about 1.5 mm to about 3.0 mm. The thicknesses of the fixation plate need not to be uniform. In some embodiments, the fixation plate can be conformable to the vertebral surfaces of the implantation sites.

In some embodiments, the spacer component can be attached to a fixation component comprising a mesh or lattice. The fixation component can also be made from a material that is the same or different from the spacer component. In some instances a fixation component and a spacer component having different materials can be beneficial because the spacer component can be configured to withstand compressive forces while the fixation component is configured to withstand primarily tension forces. The fixation component can comprise a polymer, a woven material, or a combination thereof.

In some embodiments, the flange 102 can be configured for positioning across an intervertebral space such that the upper portion 104 of the flange 102 can be adapted to contact the superior vertebra and the lower portion 106 of the flange 102 can be adapted to contact the inferior vertebra about an intervertebral space. In some embodiments, the flange 102 can be configured to contact a single vertebra about an intervertebral space, or more than two vertebrae. In some embodiments, the flange 102 can span two or more intervertebral spaces. Typically, the implant 100 can be adapted for positioning about the anterior surface of the vertebrae, along the anterior surfaces of vertebral bodies. In some instances, the flange 102 of the implant 100 can also be configured to contact other vertebral structures such as the pedicles, transverse processes, facet joints, superior and inferior articular processes and spinous processes. In still other embodiments, the implant 100 can be configured to attach to these vertebral structures without attaching or contacting the vertebral bodies.

Referring back to FIGS. 5A through 5D, each upper portion and lower portion of the fixation plate 102 can have one or more spaces or holes 112 oriented between the bone facing surface 108 and access surface 110 that are configured to accept screws and/or other attachment elements for anchoring the implant to the vertebral bone. In some embodiments, one or more bone screws 158 configured for insertion through one or more screw holes 112 in the fixation plate 102 are provided.

Each hole 112 of the flange or fixation plate 102 need not have the same configuration or size. The holes 112 can be round in cross-section and dimensioned to allow passage of a screw body therethrough while resisting passage of the screw head completely through the hole 112. In some embodiments, at least a portion of the hole 112 can have a non-round cross-section, such as an oval, square, rectangle, polygon or other closed shape. The inside surface of the holes 112 can be covered with a lubricious coating to facilitate insertion and/or movement of a screw or other attachment device through the hole.

In some embodiments, the flanged interbody device comprises a polyaryl polymer, including but not limited to PEK, PEEK, PEKK, PEKEKK or a blend thereof, and the insert comprises a titanium or titanium alloy. Other combination can also be used as is known by those with skill in the art.

C. Implantation Procedure

In some embodiments, the patient can be intubated and general anesthesia can be achieved. The patient can be prepped and draped in the usual sterile fashion. An anterior approach to the spine can be used to expose the anterior vertebral bodies. Many anterior approaches to the vertebral column are described in various medical texts such as Campbell's Operative Orthopaedics, 10th ed., edited by Canale et al., pp. 1569-1588, herein incorporated by reference. In some embodiments, the upper cervical spine can be accessed. The anterior upper cervical spine can be accessed by a transoral or retropharyngeal route, or by using a subtotal or extended maxillotomy. In other embodiments, the lower cervical spine, cervicothoracic junction, thoracic spine, thoracolumbar junction, lumbar region, lumbosacral junction, sacrum or combination of the above regions can be accessed.

The intervertebral space can be debrided. In some embodiments, the flanged interbody implant can be packed with natural or artificial bone matrix and/or other osteogenesis factors and inserted into the intervertebral space. The flange can be positioned against the anterior cervical vertebral bodies and attached with screws or anchors. The operative site can be irrigated with antibiotics and the operative field can be sutured closed. The vertebral column can be accessed and one or more intervertebral spaces can be identified and accessed. In some embodiments, two or more intervertebral spaces can be accessed, and in still other embodiments, two or more adjacent intervertebral spaces can be accessed. The operative site can be rinsed with antibiotic solution and the operative field can be closed in layers.

In another embodiment, a method for treating a spine can comprise the steps of providing an implant for treating the spine comprising two or more fixation plates, a spacer, and two or more articulation between the spacer and the two or more fixation plates, wherein the fixation plates are independently movable. The spacer can be inserted into an intervertebral space between a first vertebra and a second vertebra. One of the fixation plates can be positioned to lie generally flat on the first vertebra and can be attached to the first vertebra. A second fixation plate can be positioned in generally the opposite direction as the first fixation plate to lie generally flat on the second vertebra and can be attached to the second vertebra. Any remaining fixation plates can further be positioned to lie generally flat on the first or second vertebra and attached to the vertebra.

In some embodiments, the method for treating a spine can further comprise providing a second implant for treating the spine comprising two or more fixation plates, a spacer, and two or more articulations between the spacer and the two or more fixation plates, wherein the fixation plates are independently movable. The spacer of the second implant can be inserted into a second intervertebral space between the second vertebra and a third vertebra, wherein the second intervertebral space is next to the first intervertebral space along a vertebral column. One of the fixation plates of the second implant can be positioned to lie generally flat on the second vertebra and complementary to the second fixation plate of the first implant and can be attached to the second vertebra. In embodiments with two fixation plates, when the left fixation plate of the first implant is fixed to the second vertebra, the right fixation plate of the second implant can be attached to the second vertebra, so the left fixation plate of the first implant is positioned next to the right fixation plate of the second implant on the second vertebra. A second fixation plate of the second implant can be positioned in generally the opposite direction as the first fixation plate of the second implant to lie generally flat on the third vertebra and can be attached to the third vertebra. In another embodiment, the method for treating a spine can further comprises providing a third or additional implants for treating the spine and implanting according to the method for the second implant.

D. Pivot Plate

In some embodiments of the invention, the interbody spacer and the fixation plate can be configured to provide some degree of relative movement between each other. By providing some relative movement between the interbody spacer and fixation plate portions, the device can have improved securement to osseous structures with improved conformance to the existing anatomy at the site of implantation. FIGS. 5A through 5D depict an embodiment comprising a hinge joint 128 oriented to allow pivoting of the fixation plate 102 relative to the spacer 114. In the illustrated embodiment, the hinge joint 128 is oriented to allow pivoting in the sagittal plane. In other embodiments of the invention, the hinge joint 128 can be oriented to allow pivoting in other planes such as the transverse plane, coronal plane, or any plane in between the three planes. The joint provided between the interbody spacer 114 and the fixation plate 102 can be further configured to limit the range of movement provided. In other embodiments, the configuration of the interbody spacer 114 and/or fixation plate 102 can restrict the relative range of motion between the two components. Recesses in the fixation plate 102 or a size reduction or tapering of the interbody spacer 114 about the movement joint 128 can provide clearance to allow greater range of movement between the fixation plate 102 and the spacer 114. One of skill in the art will understand that the movement joint 128 may be configured to vary other characteristics of the movement joint, including frictional resistance or ratchet-type resistance to movement. Although the hinge joint in FIGS. 5A to 5D are depicted in a symmetric position on the interbody spacer and fixation plate, an eccentric location may be used.

Although a hinge-type movement joint is depicted in FIGS. 5A to 5D, other types of joints or connections between the interbody spacer component and fixation plate are also contemplated, including but not limited to an elastomeric joint, a ball-and-socket joint, a sliding joint, a rotatable articulation configured to allow reversible separation of the fixation plate and spacer, or one or more metallic cords embedded or attached between the fixation plate and interbody spacer to allow limited polyaxial movement.

Moreover, although a single interbody spacer 114, fixation plate 102 and movement joint 128 are depicted, other embodiments can have two or more movement joints and wherein either the fixation plate and/or interbody spacer can have a split configuration so that each split component has its own movement joint and can independently move or pivot to provide additional conformance to the existing anatomy.

In still other embodiments, the fixation plate 102 and/or interbody spacer 114 can be configured with two or more subcomponents that are provided with an intracomponent hinge or movement joint to provide better conformance of the device to the existing anatomy. For example, the fixation plate component of the device can be configured as left and right subcomponents with a hinge joint in-between. In another example, the interbody spacer can have superior and inferior subcomponents with a hinge joint therebetween to allow pivoting of the superior and inferior surfaces of the interbody spacer. Depending on the orientation of the hinge joint, the superior and inferior surfaces of the interbody spacer can pivot laterally or in an anterior-posterior direction, or any direction in-between.

E. Multi-Axial Movement Fixation Plate

Figure 6A:
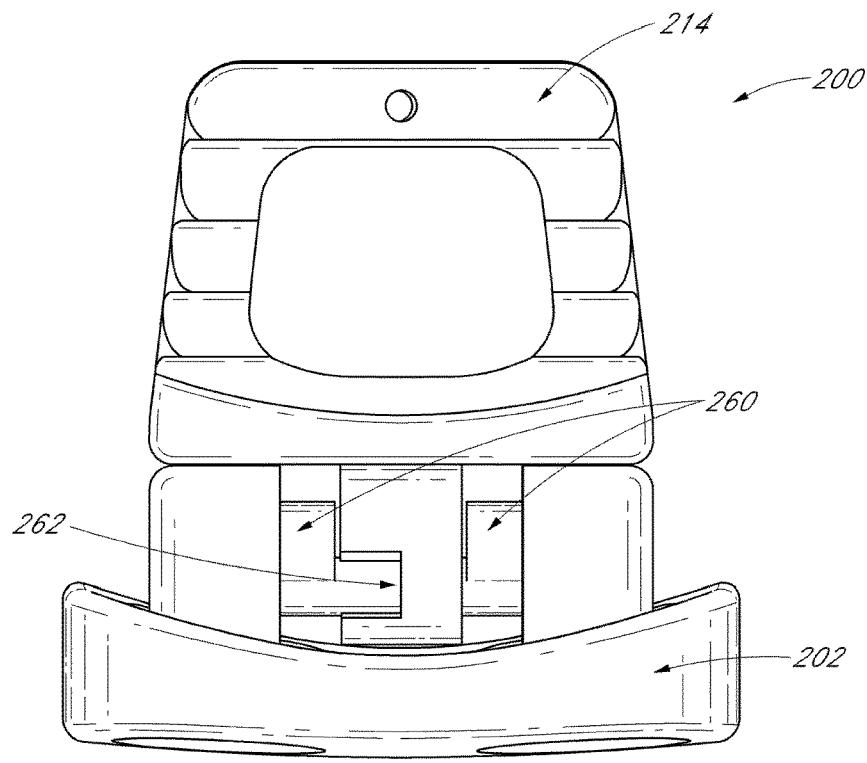
FIGS. 6A to 6D are various views of an embodiment of an integrated fixation plate and spacer device with at least two articulations.
Figure 6B:
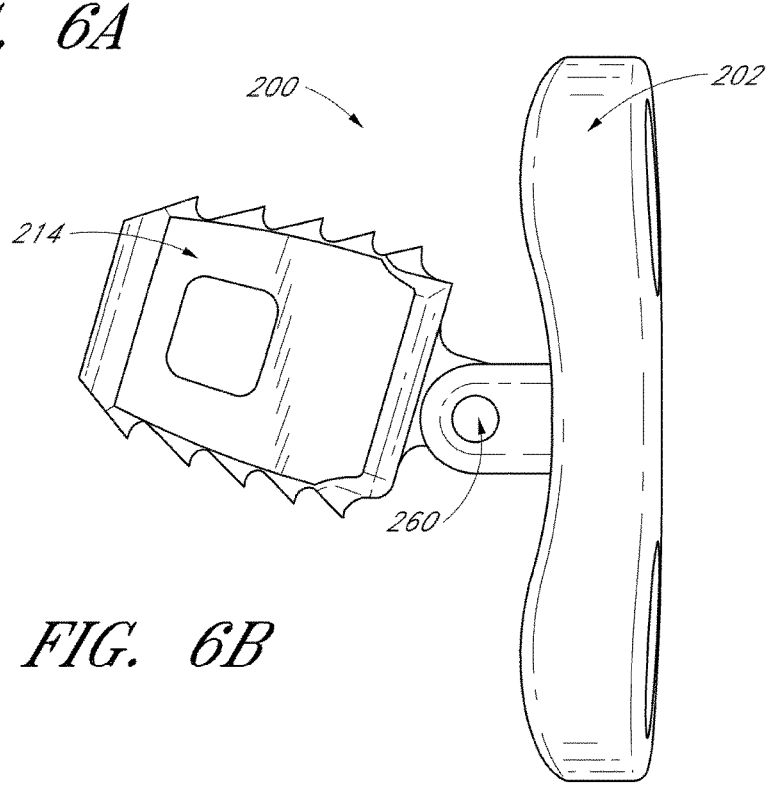
Figure 6C:
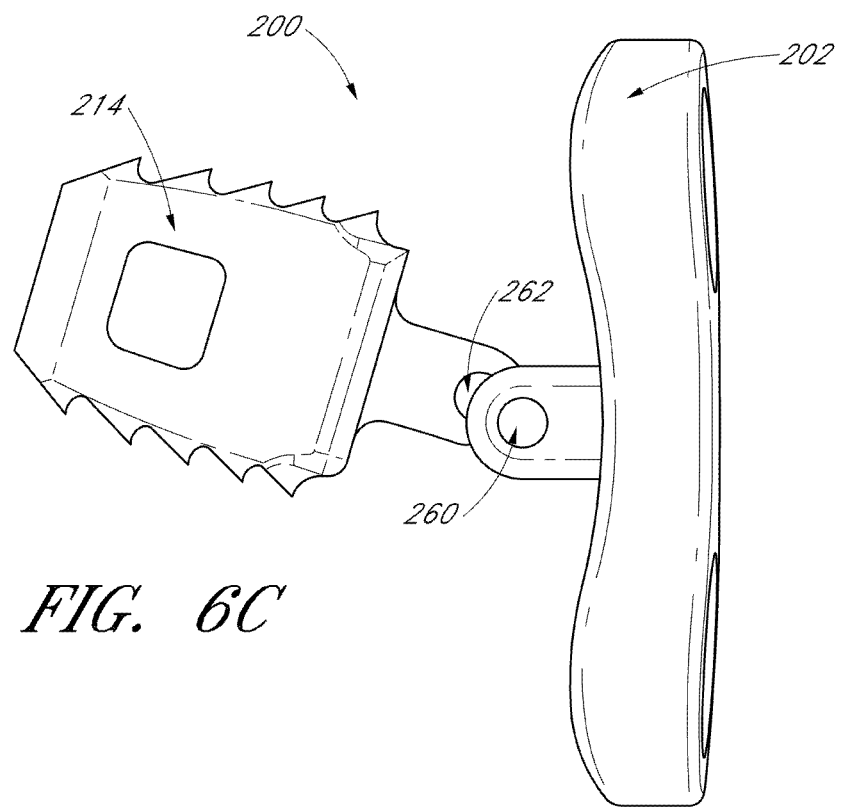
Figure 6D:
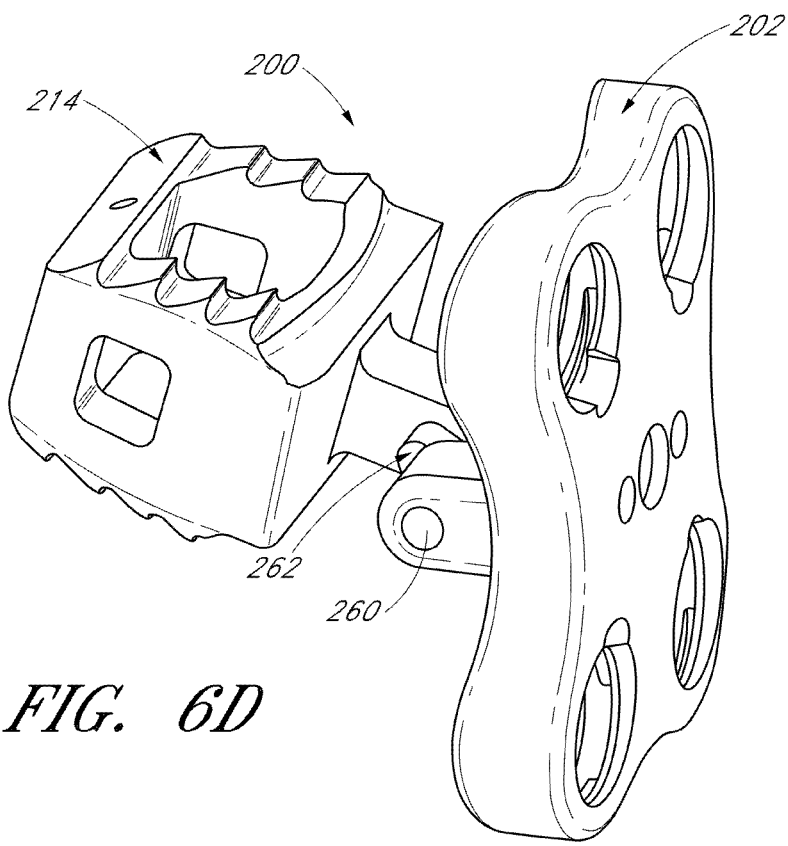

In some embodiments, multiple joints between the interbody spacer and the fixation plate can be configured to provide additional degrees of movement relative to each other. By providing adjustment of the fixation plate in multiple degrees of movement relative to the interbody spacer, securement to osseous structures can be improved while also improving conformance to the existing anatomy at the site of implantation. FIGS. 6A through 6D illustrate an implant 200 comprising a double hinge joint 260 and single hinge joint 262 disposed to allow multiple degrees of movement. The double hinge joint 260 can move in a circular cam motion about the longitudinal axis of single hinge joint 262, or in an alternative description, the single hinge joint 262 can move in a circular cam motion about the longitudinal axis of the double hinge joint 260. The two hinge configuration can allow the spacer 214 and the fixation plate 202 to move in a circular and reciprocating movement relative to each other. The combination of the double hinge joint 260 and the single hinge joint 262 can permit the relative movement in both the anterior-posterior and the superior-inferior directions. Both the interbody spacer 214 and the fixation plate 202 can also have an additional degree of pivotal movement about the hinge joints 262 and 260. FIGS. 6A and 6B illustrate the device in the configuration where the distance between the spacer 214 and the fixation plate 202 is at its minimum. FIGS. 6C and 6D illustrate the device in the configuration where the distance between the spacer 214 and the fixation plate 202 is toward its maximum.

In some embodiments, the hinge joints 260 and 262 can be oriented to allow similar movements in any plane such as the sagittal plane, transverse plane, coronal plane, or any plane in-between the three planes. In some embodiments, the hinge joints 260 and 262 provided between the interbody spacer 214 and the fixation plate 202 can be configured to limit the range of movement provided. In some embodiments, the configuration of the interbody spacer 214 and/or fixation plate 202 can restrict the relative range of motion between the two components. In some embodiments, recesses in the fixation plate 202 or a size reduction or tapering of the interbody spacer component 214 about the hinge joints 260 and 262 can allow greater range of motion. The hinge joints 260 and 262 can be configured to vary other characteristics of the movement joints, including frictional resistance or ratchet-type resistance to movement. Although the hinge joints in FIGS. 6A through 6D are depicted in a symmetric position on the interbody space and fixation plate, an eccentric location can be used.

Although hinge-type movement joints are depicted in FIGS. 6A to 6D, other types of joints or connections between the interbody spacer component and fixation plate are also contemplated, including but not limited to elastomeric joints, ball-and-socket joints, sliding joints, rotatable articulations configured to allow reversible separation of the fixation plate and the spacer, or one or more metallic cords embedded or attached between the fixation plate and interbody spacer to allow limited polyaxial movement.

The hinge-type movement joints depicted in FIGS. 6A to 6D can advantageously allows the distance between the fixation plate 202 and the spacer 214 to be adjusted by the surgeon. In this manner, a single device can be adapted to individual anatomies. This can reduce the amount of inventory needed.

F. Multiple Pivot Plates

Figure 7A:
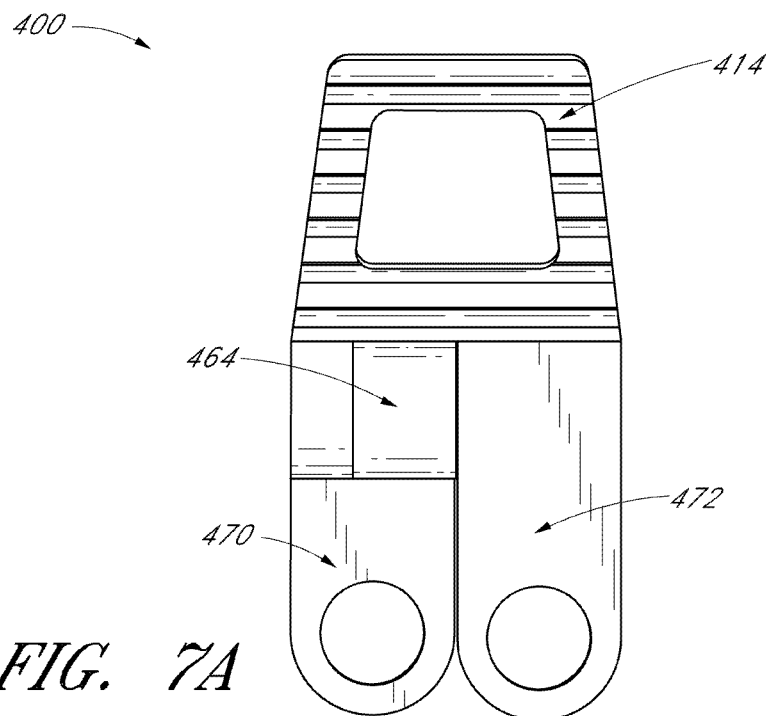
FIGS. 7A to 7D are various views of an embodiment of an integrated fixation plate and spacer device with more than one plate.
Figure 7B:
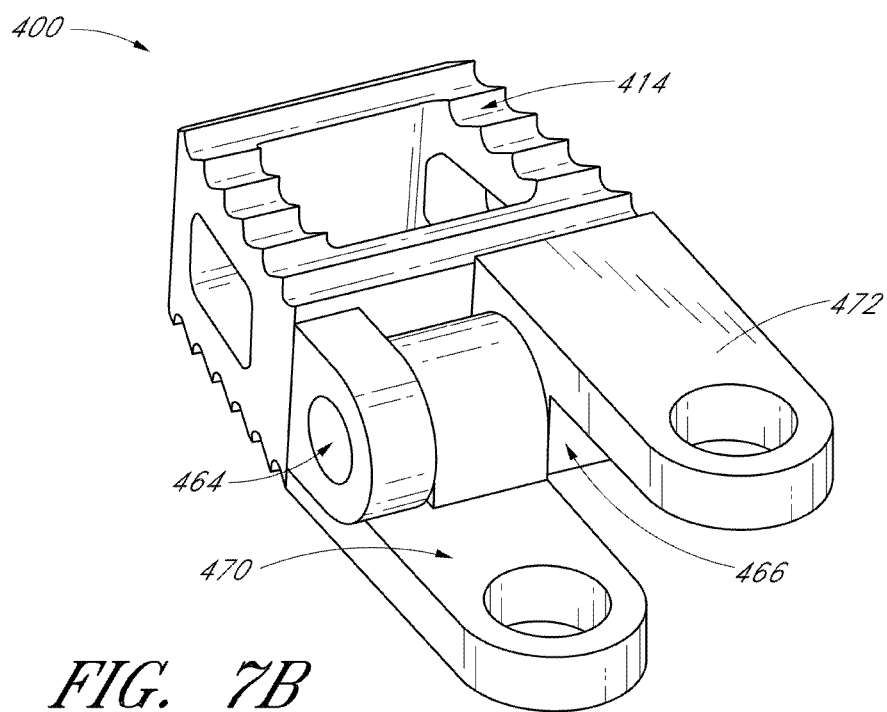
Figure 7C:
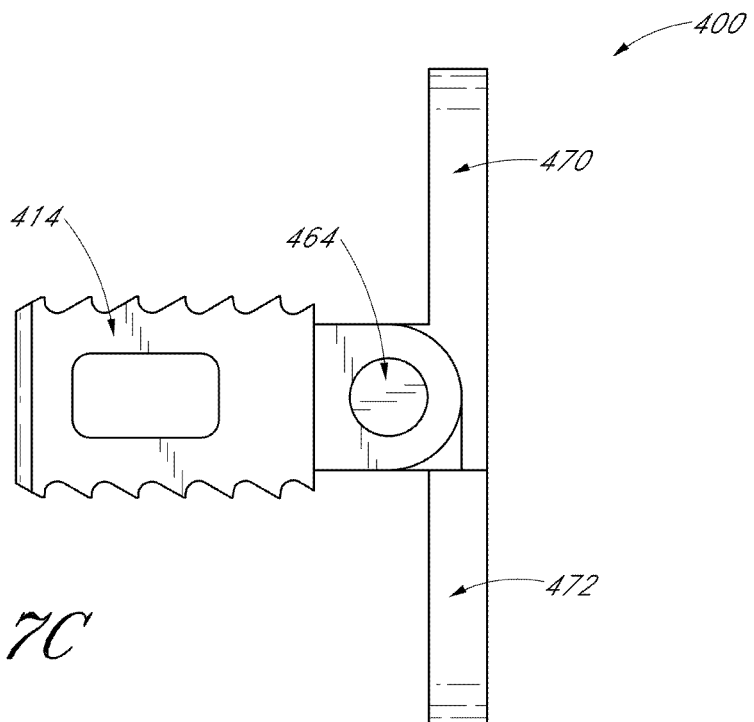
Figure 7D:
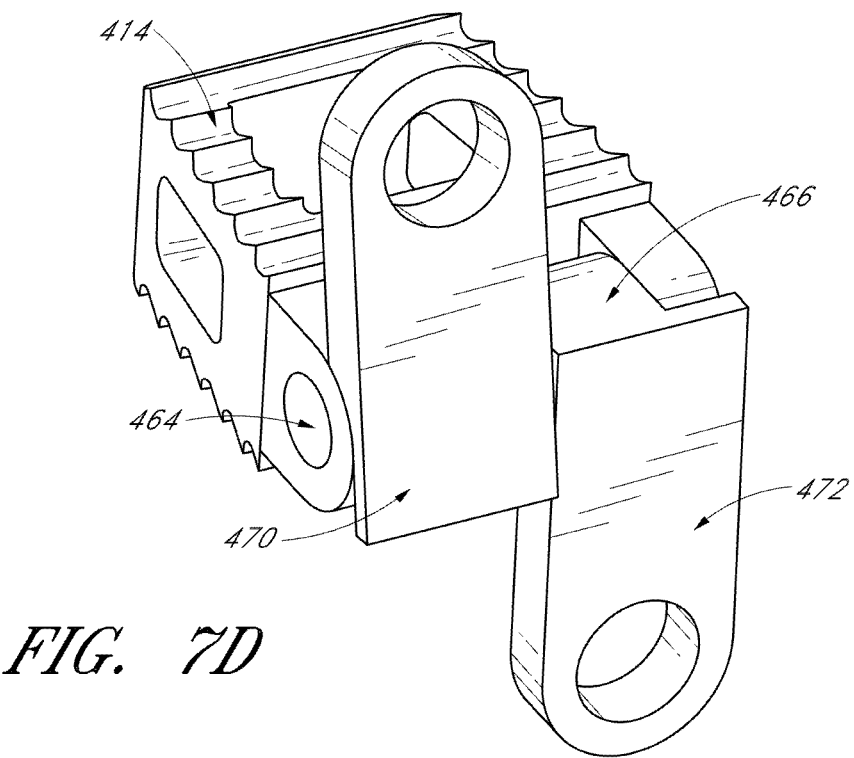

In some embodiments, the implant can comprise two or more fixation plates with independent movement joints, wherein each fixation plate is coupled to a separate movement joint that can independently move or pivot to provide additional conformance to the existing anatomy. FIGS. 7A through 7D depict such an implant 400, comprising an interbody spacer 414, a first fixation plate 470 coupled to the interbody spacer 414 by a first hinge joint 464, and a second fixation plate 472 coupled to the interbody spacer 414 by a second hinge joint 466. The hinge joints 464 and 466 can allow the pivotal movement between the interbody spacer 414 and the two fixation plates 470 and 472. In some embodiments, the fixation plates 470 and 472 can be pivoted to a predetermined position, such as generally parallel to the interbody spacer 414, so that the spacer 414 can present a low profile, as illustrated in FIGS. 7A and 7B. This configuration can be advantageous for insertion of the device into an intervertebral space in the body. In some embodiments, the fixation plates 470 and 472 can be pivoted so that they extend away from the interbody spacer 414, which can also advantageously serve insertion of the device. In some embodiments, the first fixation plate 470 can be pivoted to a position generally perpendicular to the interbody spacer 414, and coupled with a first vertebra, and the second fixation plate 472 can be pivoted in a direction opposite to the first fixation plate 470 to a position generally perpendicular to the interbody spacer 414 and coupled with a second vertebra. FIGS. 7C and 7D illustrate the implant 400 in this configuration. In some embodiments, the first and second fixation plates 470 and 472 can be independently pivoted to various positions at certain angles relative to the interbody spacer 414 for coupling with two adjacent vertebras.

In other embodiments, the hinge joints 464 and 466 can be oriented to allow pivoting in any plane such as the sagittal plane, transverse plane, coronal plane, or any plane in-between the three planes. The joints provided between the interbody spacer 414 and the fixation plates 470 and 472 can be further configured to limit the range of movement provided. In some embodiments, the configuration of the interbody spacer 414 and/or fixation plates 470 and 472 can restrict the relative range of motion between the components. In some embodiments, recesses in the fixation plates 470 and 472 or a size reduction or tapering of the interbody spacer component 414 about the movement joints 464 and 466 can allow greater range of motion between the components. The movement joints 464 and 466 can be configured to vary other characteristics of the movement joint, including frictional resistance or ratchet-type resistance to movement. In some embodiments, the joints 464 and 466 can each comprise multiple joints to provide multi-axial motion, as described above.

In other embodiments, the implant can include more than two fixation plates, with each fixation plate able to pivot to a position generally perpendicular or at any angle to the interbody spacer and couple with the first or second vertebra. Although the hinge joints in FIGS. 7A through 7D are depicted in a symmetric position on the interbody spacer and fixation plates, an eccentric location can be used.

Although a hinge-type movement joint is depicted in FIGS. 7A through 7D, other types of joints or connections between the interbody spacer component and fixation plates are also contemplated, including but not limited to elastomeric joints, ball-and-socket joints, sliding joints, rotatable articulations configured to allow reversible separation of the fixation plate and spacer, or one or more metallic cords embedded or attached between the fixation plate and interbody spacer to allow limited polyaxial movement. The above described spacer is particularly useful in embodiments in which a superior and inferior vertebrae are separated using pins or other devices. For example, in certain applications (e.g., in the cervical spine) elongate pins can be implanted into superior and inferior vertebrae and used as anchors to separate the vertebra from each other. The elongate pins can be implanted in an offset orientation, for example wherein a first elongate pin can be implanted on the left portion of a first vertebra and the second elongate pin can be implanted on the right portion of a second vertebra. The above described embodiments allow the flanges 470, 472 to be pivoted into the spaces on the vertebra not occupied by the pins. That is, one of the fixation plates can be positioned to lie generally flat on the right portion of the first vertebra and can be attached to the first vertebra. A second fixation plate can be positioned in generally the opposite direction as the first fixation plate to lie generally flat on the left portion of the second vertebra and can be attached to the second vertebra.

G. Alternative Screw Locks

In addition to the embodiments of the screw retaining assemblies described above, other screw retaining assemblies are also contemplated and can be used with the interbody fusion devices previously described. The other screw retaining assemblies described below can also be used with other types of orthopedic and medical devices, as well as non-medical applications, including but not limited to construction, home improvement, consumer appliance, electronic device and other applications.

1. Screw Retainer with Pivot Surface

Figure 8:
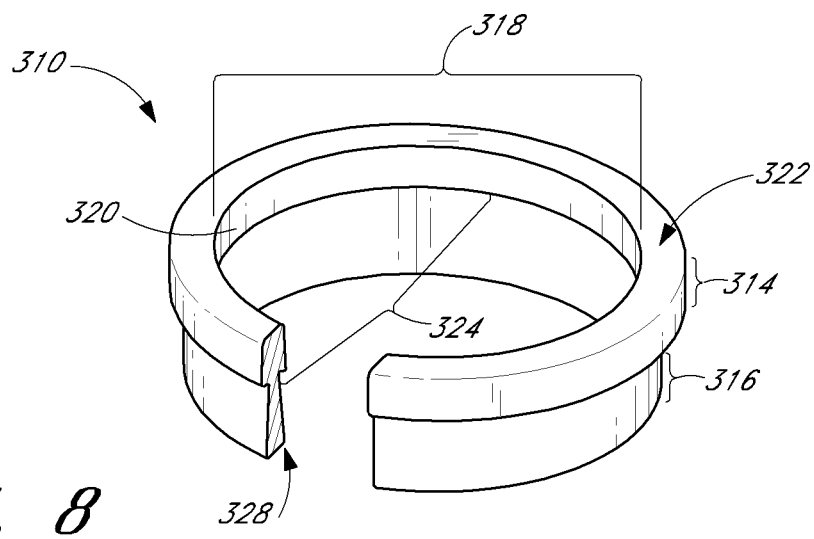
FIG. 8 is an isometric elevational view of an embodiment of a fastener retaining assembly.
Figure 9:
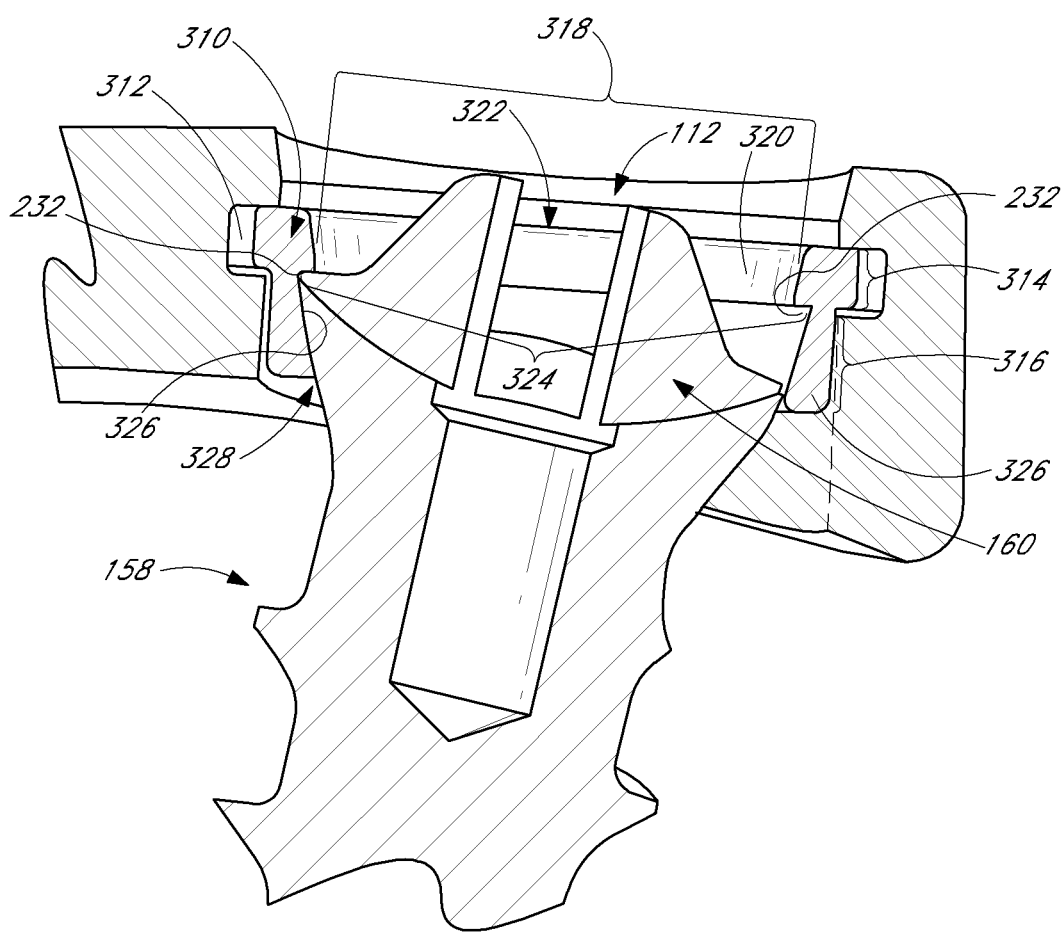
FIG. 9 is a cross-sectional view of a fixation device with the fastener retaining assembly of FIG. 8 and an inserted screw.

FIGS. 8 and 9 depict some embodiments comprising an expandable fastener retaining ring 310 residing partially within an expansion groove 312 of a fastener lumen 112 and partially within the fastener lumen 112 itself. The retaining ring 310 can have a reduced configuration and an expanded configuration but can be biased to the reduced configuration. The retaining ring 310 can have a retaining segment 314 and a pivot segment 316. Referring to FIG. 9, the retaining segment 314 can have an enlarged outer diameter that is adapted to fit in an expansion groove 312. In the expanded configuration of the retaining ring 310, the retaining segment 314 can further expand into the expansion groove 312, thereby increasing the inner diameter 318 of the retaining segment 314. The inner diameter 318 of the retaining segment 314 can have a sloped inner surface 320 that narrows from the proximal opening 322 of the retaining ring 310. The sloped surface 320 can facilitate expansion of the retaining segment 314 as a fastener 158 is inserted through it. Once the fastener head 160 has passed through the retaining segment 314 of the retaining ring 310, the inner diameter 324 of the polyaxial segment 316 of the retaining ring 310 can be larger, allowing the fastener head 160 to reside in the retaining ring 310 without exerting an expansion force against the retaining ring 310. This can allow the retaining ring 310 to at least partially, if not completely, revert back to its reduced configuration. If backout forces are exerted on the fastener head 160, the fastener head 160 can abut a generally perpendicular retaining surface 232 located at the transition from the inner diameters 318, 324 of the retaining and polyaxial segments 314, 316 of the ring 310 and can resist fastener head 160 backout.

The polyaxial segment 316 of the retaining ring 310 can comprise a sloping reduced diameter 326 towards the distal opening 328 of the retaining ring 310, such that the smallest diameter of the polyaxial segment 316 can be smaller than the largest diameter of the fastener head 160 and can prevent or resist the fastener head 160 from passing completely through the retaining ring 310. The slope of the cross-section through the retaining ring can be linear, curved, toothed or jagged or any other sloped surface.

2. Fastener Head Embedded Expansion Lock

Figure 10A:
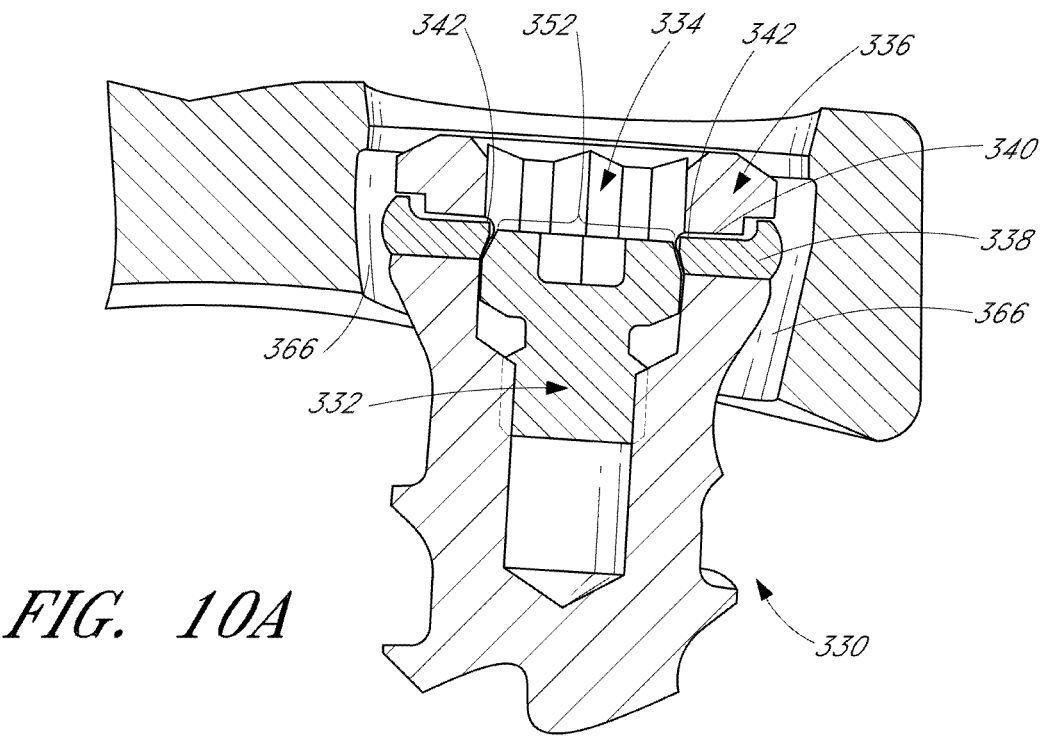
FIG. 10A is a cross-sectional view of another embodiment of a fastener with an expansion ring.
Figure 10B:
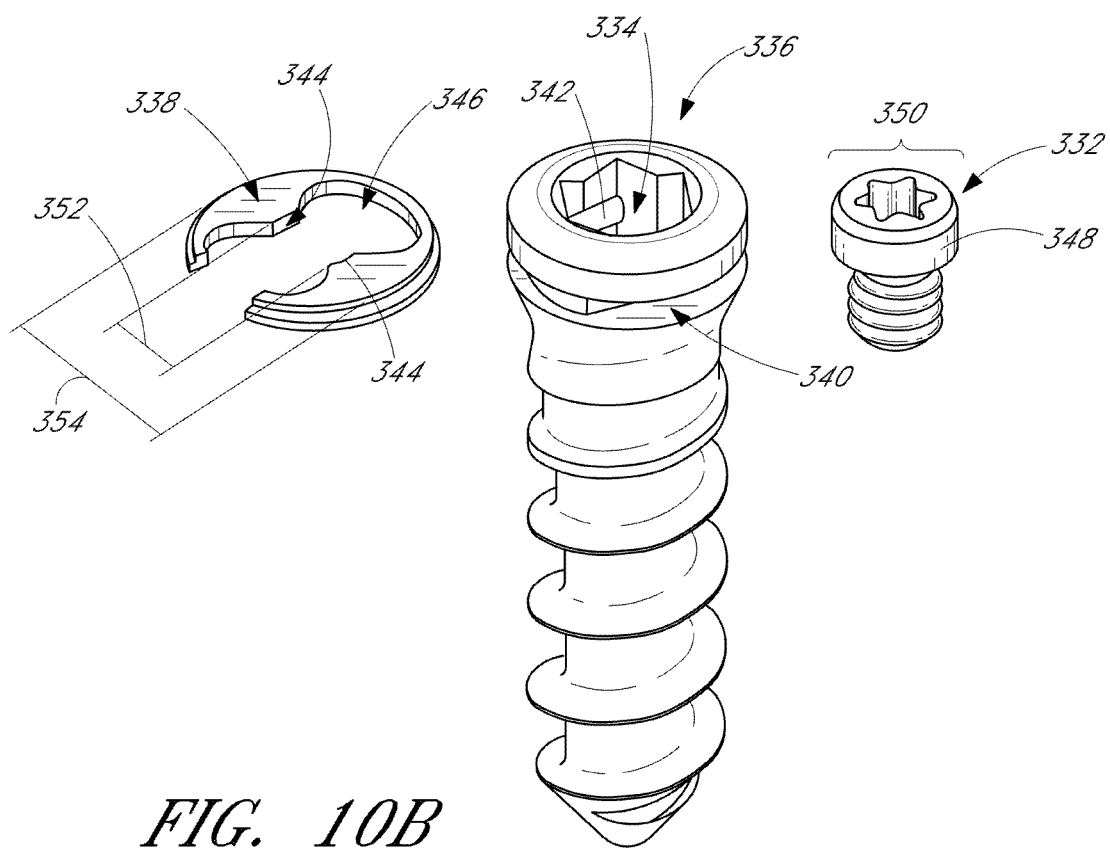
FIG. 10B is an exploded view of the fastener and expansion ring in FIG. 10A.

In some embodiments, illustrated in FIGS. 10A and 10B, the fastener 330 can comprise a secondary screw 332 and screw lumen 334 within the fastener head 336. An expandable ring 338 or disc, having a reduced and an expanded configuration, is provided within a groove 340 about the fastener head 336, with the expandable ring or disc biased to the reduced configuration. The groove 340 can be contiguous with screw lumen 334 of the fastener head 336 at one or more openings 342, such that the portion 344 of the inner surface 346 of the expandable ring 338 or disc partially protrudes into the screw lumen 334 when the expandable ring 338 or disc is in the reduced configuration. The secondary screw 332 of the fastener 330 can have an expansion section, typically the head 348 of the secondary screw 332, which can have an outer diameter 350 that is greater than the distance 352 within the screw lumen 334 where the expansion ring 338 or disc protrudes into the screw lumen 334. When the expansion section 348 of the secondary screw 332 is not in contact with the inner protruding portions 344 of the expandable ring 338 or disc, the expandable ring 338 or disc is able to remain in the reduced configuration. When the expansion section 348 of the secondary screw 332 is fully positioned against the protruding portions 344 of the expandable ring 338 or disc, it can act against the expandable ring 338 or disc and can cause the expandable ring 338 or disc to enlarge to its expanded configuration. In the expanded configuration, the outer diameter 354 of the expandable ring 338 or disc can be greater than the largest outer diameter of the remaining portions of the fastener 330. In the reduced configuration, the outer diameter of expandable ring or disc may or may not radially extend from out of the groove.

Figure 11:
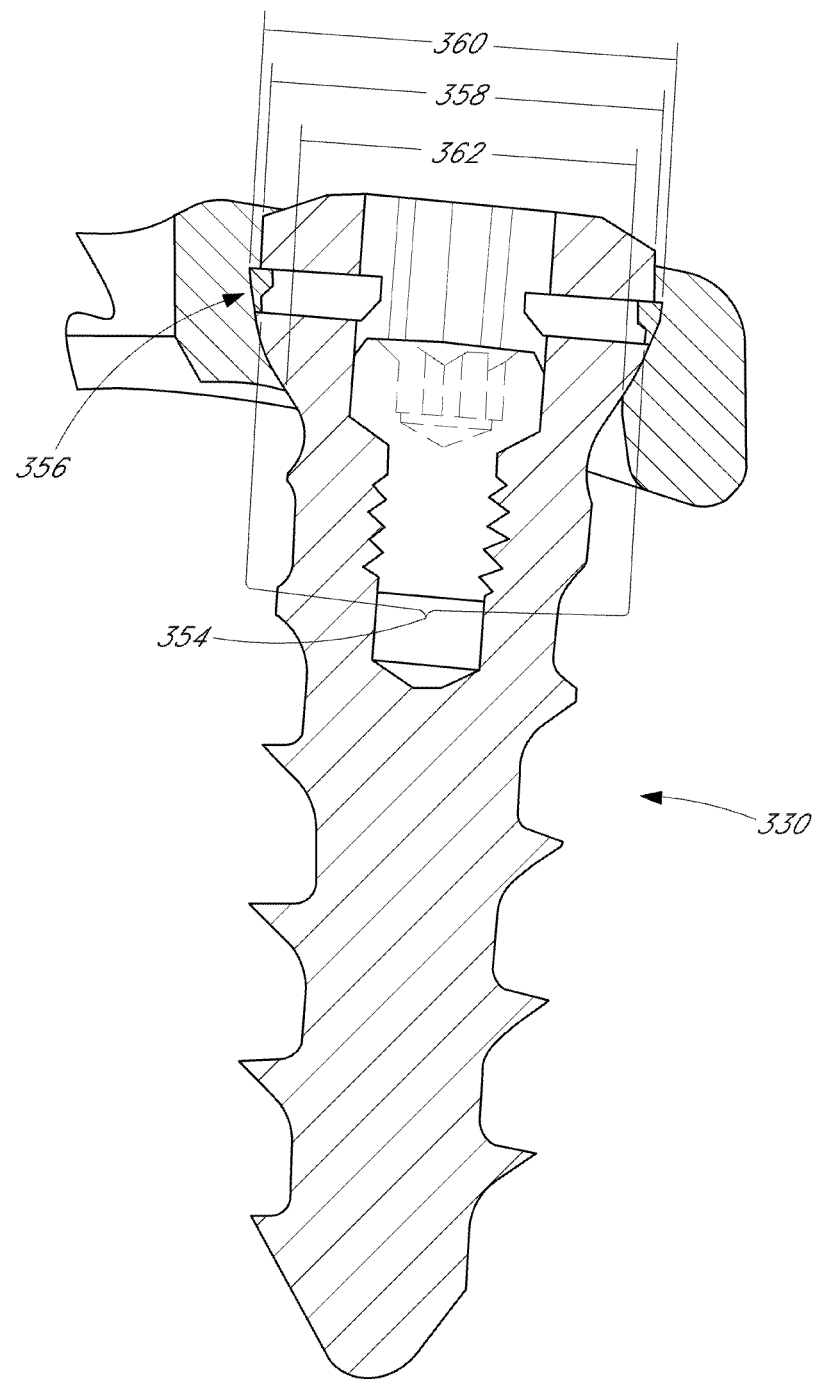
FIG. 11 is a cross-sectional view of an embodiment of a fastener with an expansion ring.

Referring to FIG. 11, the fastener 330 is preferably used in devices having one or more fastener lumens 356 with a proximal diameter 358, middle diameter 360 and distal diameter 362, wherein the proximal diameter 358 is greater than the distal diameter 362 but less than the middle diameter 360, and wherein the proximal diameter 358 is less than the outer diameter 364 of the expandable ring 354 or disc in the reduced configuration. The outer diameter of the expandable ring 338 or disc, in the expanded configuration, can be larger than the proximal diameter 358 of the fastener lumen 356, thereby preventing or resisting backout of the fastener 330. In some embodiments, as shown in FIG. 10A, the screw lumen can be lined by an hole insert 366 having a similar relationship of its proximal, middle and distal diameters. A hole insert 366 can be preferred, for example, when the orthopedic device utilizing the fastener system comprises a material that may exhibit wear from the metallic fasteners. A hole insert 366 can be provided to protect against such wear.

Referring again to FIG. 10A, the screw lumen 334 of the fastener 330 can extend distally from the openings 342 contiguous with the fastener head groove 340 to allow the secondary screw 332 to completely reside within the screw lumen 334 in a position distal to the screw lumen openings 342 and inner protrusions 344 of the expandable ring 338 or disc. This feature can allow the fastener 330 to be attached to the desired structure without having to later insert the secondary screw 332 into the fastener 330 to enlarge the expandable ring 338 or disc. Instead, once the fastener 330 is attached to the desired structure, the secondary screw 332 need only be moved proximally in the screw lumen 334 to act against the expandable ring 338 or disc and enlarge the expandable ring 338 or disc to its expanded configuration and to retain the fastener in place. By allowing the attachment of the fastener 330 with the secondary screw 332 already in place, the use of fastener 330 in cramped or limited access areas, such as the attachment of a cervical fusion plate or interbody fusion device, need not attempt to maintain a tiny secondary screw 332 on the end of an attachment device while attempting to align the tiny secondary screw 332 with the screw lumen 334 of the fastener head. The user of the fastener 330 only has to align the screwdriver of the secondary screw to the secondary screw in order to manipulate it.

H. Conclusion

Although the present invention has been described in relation to various exemplary embodiments, various additional embodiments and alterations to the described embodiments are contemplated within the scope of the invention. Thus, no part of the foregoing description should be interpreted to limit the scope of the invention as set forth in the following claims. For all of the embodiments described above, the steps of the methods need not be performed sequentially.

What is claimed is:

1. An implant for treating the spine, comprising:
   a fixation plate having an access surface and a bone facing surface;
   a spacer; and
   at least two articulations between the spacer and the bone facing surface of the fixation plate, a first articulation allowing for 360 degrees of movement between the spacer and an intermediate member, and a second articulation allowing for movement between the intermediate member and the fixation plate, each articulation comprising a separate axis of rotation, wherein the at least two articulations are configured to allow multiple degrees of rotation.

2. The implant for treating the spine as in claim 1, wherein the at least two articulations provide for anterior-posterior movement between the spacer and the fixation plate.

3. The implant for treating the spine as in claim 1, wherein an articulation of the at least two articulations is a hinge joint.

4. The implant for treating the spine as in claim 3, wherein the hinge joint has a joint axis that does not intersect the fixation plate.

5. The implant for treating the spine as in claim 3, wherein the hinge joint has a joint axis configured to be perpendicular to a longitudinal axis of a vertebral column when implanted.

6. The implant for treating the spine as in claim 1, wherein the axis of rotation of at least one articulation does not intersect the fixation plate.

7. The implant for treating the spine as in claim 1, wherein the axis of rotation of at least one articulation is parallel to the fixation plate.

8. The implant for treating the spine as in claim 1, wherein at least one articulation is configured to allow reversible separation of the fixation plate and spacer.

9. The implant for treating the spine as in claim 1, wherein the at least two articulations comprise a single hinge joint and a double hinge joint.

10. The implant for treating the spine as in claim 9, wherein the double hinge joint is configured to move with 360 degrees of movement about the longitudinal axis of the single hinge joint.

11. The implant for treating the spine as in claim 1, wherein the at least two articulations are configured to allow the spacer and the fixation plate to move in a reciprocating movement relative to each other.

12. The implant for treating the spine as in claim 1, wherein the at least two articulations are configured to allow relative movement in both the anterior-posterior and the superior-inferior directions.

13. An implant for treating the spine, comprising:
a fixation plate having an access surface and a bone facing surface, an upper portion and a lower portion;
a spacer;
at least one member interconnecting the fixation plate and the spacer;
at least one articulation between the fixation plate and the at least one member to allow movement about a first axis; and
at least one articulation between the spacer and the at least one member to allow movement about a second axis;
wherein the articulations provide for 360 degrees of movement between the at least one member and the spacer, and movement between the at least one member and the fixation plate;
wherein in a first configuration, the distance between the fixation plate and the spacer is at a minimum;
wherein in a second configuration, the distance between the fixation plate and the spacer is at a maximum.

14. The implant for treating the spine as in claim 13, wherein an articulation of the at least one articulation between the fixation plate and the at least one member is a hinge joint or wherein an articulation of the at least one articulation between the spacer and the at least one member is a hinge joint.

15. The implant for treating the spine as in claim 14, wherein at least one of the hinge joints has a joint axis that does not intersect the fixation plate.

16. The implant for treating the spine as in claim 14, wherein at least one of the hinge joints has a joint axis configured to be generally perpendicular to a longitudinal axis of a vertebral column when implanted.

17. The implant for treating the spine as in claim 13, wherein an articulation of the at least one articulation between the fixation plate and the at least one member is a rotatable articulation comprising an axis of rotation or wherein an articulation of the at least one articulation between the spacer and the at least one member is a rotatable articulation comprising an axis of rotation.

18. The implant for treating the spine as in claim 17, wherein the axis of rotation of the rotatable articulation does not intersect the fixation plate.

19. The implant for treating the spine as in claim 17, wherein the axis of rotation of the rotatable articulation is parallel to the fixation plate.

20. The implant for treating the spine as in claim 17, wherein the rotatable articulation is configured to allow reversible separation of the fixation plate and spacer.

21. The implant for treating the spine as in claim 13, wherein the first axis and the second axis are parallel.

22. The implant for treating the spine as in claim 13, wherein the first axis and the second axis extend through the at least one member interconnecting the fixation plate and the spacer.

23. The implant for treating the spine as in claim 13, wherein the articulations comprise a single hinge joint and a double hinge joint.

24. A method for treating a spine, comprising:
providing the implant of claim 1, wherein the fixation plate further comprises an upper portion and a lower portion, wherein in a first configuration, the distance between the fixation plate and the spacer is at a minimum, wherein in a second configuration, the distance between the fixation plate and the spacer is at a maximum;
adjusting the implant to any configuration between, or including, the first configuration and second configuration;
inserting the spacer into an intervertebral space between a first vertebra and a second vertebra;
attaching the upper portion of the fixation plate to the first vertebra; and
attaching the lower portion of the fixation plate to the second vertebra.

* * * * *